United States Patent
Liu et al.

(10) Patent No.: US 12,269,819 B2
(45) Date of Patent: Apr. 8, 2025

(54) SMALL MOLECULE INHIBITORS OF GALECTIN-3

(71) Applicant: BRISTOL-MYERS SQUIBB COMPANY, Princeton, NJ (US)

(72) Inventors: Chunjian Liu, Pennington, NJ (US); Jianxin Feng, Bensalem, PA (US); Pratik Devasthale, Plainsboro, NJ (US); Natesan Murugesan, Princeton Junction, NJ (US); Bruce A. Ellsworth, Princeton, NJ (US); Alicia Regueiro-Ren, New Hope, PA (US); Susheel Jethanand Nara, Mumbai (IN); Prasada Rao Jalagam, Bangalore (IN); Manoranjan Panda, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 776 days.

(21) Appl. No.: 17/601,942

(22) PCT Filed: Apr. 8, 2020

(86) PCT No.: PCT/US2020/027203
§ 371 (c)(1),
(2) Date: Oct. 7, 2021

(87) PCT Pub. No.: WO2020/210308
PCT Pub. Date: Oct. 15, 2020

(65) Prior Publication Data
US 2022/0144818 A1    May 12, 2022

Related U.S. Application Data

(60) Provisional application No. 62/831,753, filed on Apr. 10, 2019.

(51) Int. Cl.
| | |
|---|---|
| *C07H 17/02* | (2006.01) |
| *C07D 405/04* | (2006.01) |
| *C07D 405/14* | (2006.01) |
| *C07D 409/14* | (2006.01) |
| *C07D 417/14* | (2006.01) |

(52) U.S. Cl.
CPC ......... *C07D 417/14* (2013.01); *C07D 405/04* (2013.01); *C07D 405/14* (2013.01); *C07D 409/14* (2013.01); *C07H 17/02* (2013.01)

(58) Field of Classification Search
None
See application file for complete search history.

(56) References Cited

FOREIGN PATENT DOCUMENTS

| WO | 2018209255 A1 | 11/2018 | |
|---|---|---|---|
| WO | WO-2018209276 A1 * | 11/2018 | ......... A61K 31/4439 |
| WO | 2019067702 A1 | 4/2019 | |

* cited by examiner

*Primary Examiner* — Traviss C McIntosh, III
(74) *Attorney, Agent, or Firm* — Jing G. Sun

(57) ABSTRACT

The present disclosure relates to compounds of Formula (I) or (II), which inhibit Gal-3, and include pharmaceutically acceptable salts, compositions comprising such compounds, and methods using and making such compounds and compositions.

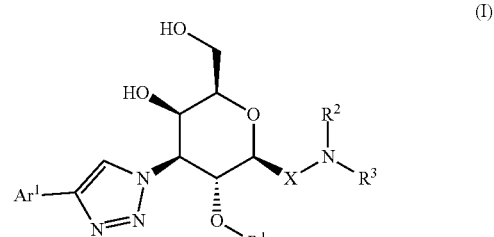

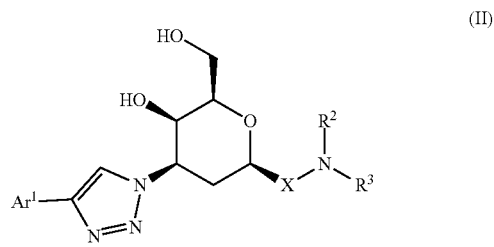

13 Claims, No Drawings

SMALL MOLECULE INHIBITORS OF GALECTIN-3

CROSS-REFERENCE TO RELATED APPLICATIONS

This application is a 371 of International Application No. PCT/US2020/027203 filed on Apr. 8, 2020, which claims the priority benefit of U.S. Provisional Application No. 62/831,753, filed Apr. 10, 2019; the content of which is herein incorporated by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involvement of Gal-3 in the development of fibrotic process in multiple organs such as lung (Am J. Respir. Crit. Care Med. 185: 537-546), liver (PNAS 103: 5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319, WO2014067986 and WO2018209255.

DESCRIPTION OF THE INVENTION

The present disclosure relates to compounds of the present invention, which inhibit Gal-3, and include pharmaceutically acceptable salts, compositions comprising such compounds, and methods using and making such compounds and compositions.

In a 1st aspect, the present invention provides, inter alia, a compound of Formula (I) or (II):

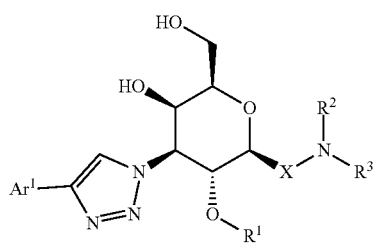
(I)

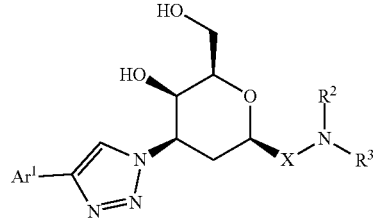
(II)

or a pharmaceutically acceptable salt thereof, wherein:
X is independently selected from —C(O)—, —CH$_2$—, and —CH$_2$C(O)—;
Ar$^1$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;
R$^1$ is independently selected from H, C$_{1-4}$ alkyl, and C$_{1-4}$ haloalkyl;
R$^2$ is independently H or C$_{1-4}$ alkyl;
R$^3$ is independently selected from Are, —(CH$_2$)$_{1-2}$Ar$^2$, and —CH$_2$CH$_2$NR$^4$Ar$^2$;
Ar$^2$ is independently selected from phenyl,

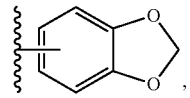

and heteroaryl including from 5 to 10 ring atoms, wherein from 1 to 4 ring atoms are each independently selected from N, N(R$^5$), O, and S; and wherein each ring moiety is substituted with 0 to 4 substituents selected from OH, cyano, halogen, C$_{1-4}$ alkyl, C$_{1-4}$ haloalkyl, C$_{1-4}$ alkoxy, C$_{1-4}$ haloalkoxy, N(C$_{1-4}$ alkyl)$_2$, —SO$_2$(C$_{1-4}$ alkyl), —OPh, —OBn, C$_{3-6}$ cycloalkyl, and phenyl substituted with 0 to 1 substituent selected from cyano, halogen, C$_{1-4}$ alkyl, C$_{1-4}$ haloalkyl, C$_{1-4}$ alkoxy, C$_{1-4}$ haloalkoxy, —NH$_2$, —NH(C$_{1-4}$ alkyl), and —N(C$_{1-4}$ alkyl)$_2$;
R$^4$ is independently H or C$_{1-4}$ alkyl; and
R$^5$ is independently H or C$_{1-4}$ alkyl.

In a 2nd aspect, within the scope of the 1st aspect, wherein the compound is of Formula (Ia):

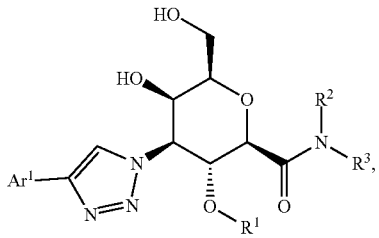
(Ia)

or a pharmaceutically acceptable salt thereof.

In a 3rd aspect, within the scope of the 1st or 2nd aspect, wherein the compound is of Formula (I) or (Ia), or a pharmaceutically acceptable salt thereof, wherein:
Ar$^1$ is independently phenyl or naphthyl; and wherein each ring moiety is substituted with 1 to 3 substituents selected from cyano, halogen, C$_{1-4}$ alkyl, and C$_{1-4}$ alkoxy;

$R^1$ is independently H or $C_{1-4}$ alkyl; and
$Ar^2$ is independently selected from phenyl,

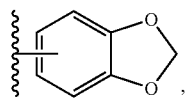

pyridinyl, benzothiophenyl, benzothiazolyl, N—($C_{1-4}$ alkyl)-indazolyl, and quinolinyl; and wherein each ring moiety is substituted with 0 to 4 substituents selected from OH, cyano, halogen, $C_{1-4}$ alkyl, $C_{1-4}$ alkoxy, $C_{1-4}$ haloalkyl, $C_{1-4}$ haloalkoxy, N($C_{1-4}$ alkyl)$_2$, —SO$_2$($C_{1-4}$ alkyl), —OPh, and —OBn.

In a 4th aspect, within the scope of the 1st to 3rd aspects, wherein: $Ar^1$ is independently selected from:

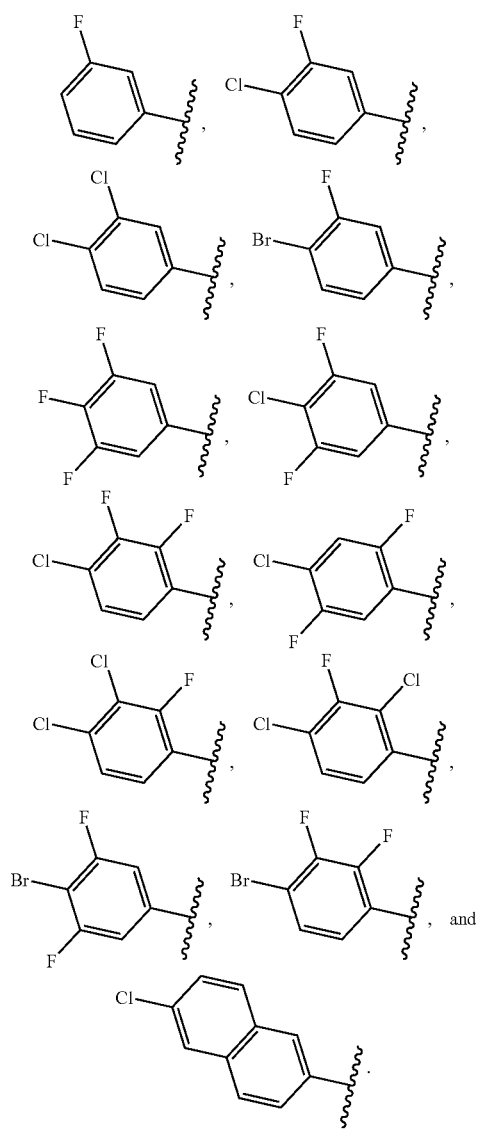

In a 5th aspect, within the scope of the 1st to 4th aspects, wherein: $R^3$ is independently selected from $Ar^2$, —(CH$_2$)$_{1-2}$Ar$^2$, and —CH$_2$CH$_2$NR$^4$Ar$^2$; $Ar^2$ is independently selected from:

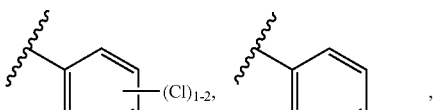
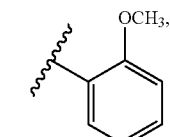
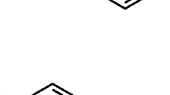
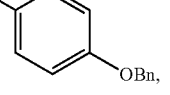
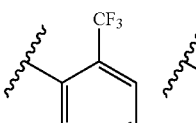
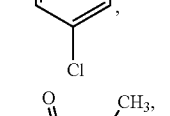
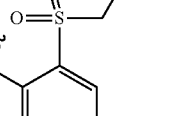
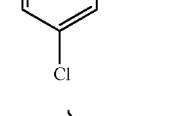
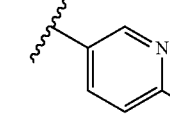
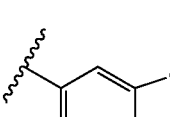
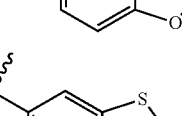
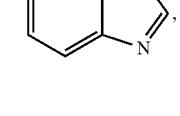
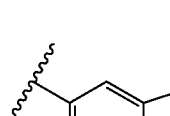
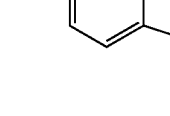

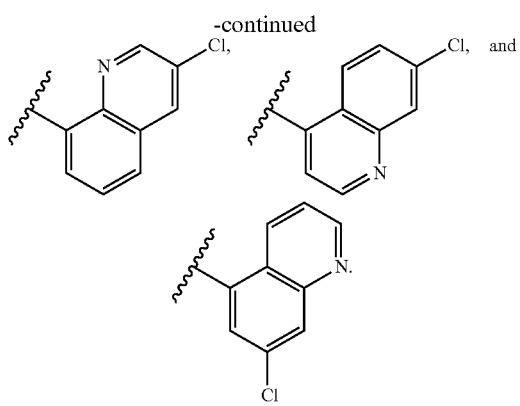

In a 6th aspect, within the scope of the 1st to 5th aspect, wherein:

$R^1$ is independently H or $CH_3$;
$R^2$ is independently selected from: H, $CH_3$, —$CH_2CH_3$, and —$CH(CH_3)_2$; and
$R^4$ is independently H or $CH_3$.

In another aspect, within the scope of any of the 1st to 6th aspects, wherein $R^1$ is H.

In another aspect, within the scope of any of the 1st to 6th aspects, wherein $R^1$ is $CH_3$.

In another aspect, the invention provides a compound selected from the exemplified examples or a pharmaceutically acceptable salt thereof.

In another aspect, the invention provides a compound selected from the Examples 1 to 44 and B1 to B25 or a pharmaceutically acceptable salt thereof.

In another aspect, the invention provides a compound selected from the Examples 1 to 44 or a pharmaceutically acceptable salt thereof.

In another aspect, the invention provides a compound selected from the Examples B1 to B25 or a pharmaceutically acceptable salt thereof.

Unless specified otherwise, these terms have the following meanings. "Alkyl" means a straight or branched alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Gal 3 HTRF Assay
ASSAY BUFFER Composition: 25 mM HEPES, 100 mM NaCl, 0.005% Tween 20, 0.05% BSA prepared in sterile water (all reagents from Sigma).
Controls:
Positive Control: 100% DMSO (1 μL)+His-tagged hGal-3 (20 μL)+B-ASF (20 μL)+Anti-His Terbium Antibody (5 μL)+Strep d2 Antibody (5 μL).
Negative Control: 100% DMSO (1 μL)+His-tagged hGal-3 (20 μL)+Anti His Terbium Antibody (5 μL)+Strep d2 Aantibody (5 μL).
Stocks Preparation:

| | Stock Conc. | Intermediate Conc. | Final Assay Conc. | Volume |
|---|---|---|---|---|
| His-tagged hGal-3 | 49.82 μM or can vary batch to batch | 2.525X | 15 nM | 20 μL |
| B-ASF | 25 μM | 2.525X | 15 nM | 20 μL |
| Compounds | 20 mM in 100% DMSO | Various concentration 100% DMSO | Various concentration 2% DMSO | 1 μL |
| Anti-His Tb Ab | 5.75 μM | (10X) 10 nM | 1 nM | 5 μL |
| Strep d2 | 16.67 μM | (10X) 200 nM | 20 nM | 5 μL |
| Total Assay volume | | | | 51 μL |

PROTOCOL: The Gal-3 assays were performed in 384 white Opti plates in three replicates at room temperature with gentle shaking at 250-300 rpm From the original stocks, 2.525× working stock concentrations of His-tagged recombinant human Gal-3 (hGal-3) and that of B-ASF were prepared. From the working stock, 20 µL of hGal-3 (15 nM) and 20 µL B-ASF (15 nM) were added to the plates. In Negative Control, only hGal-3 was added. A concentration range of 50× working stocks were prepared for the compounds in 100% DMSO. Aliquots of 1 µL of the compounds were added to the wells and pre-incubated with 20 µL hGal-3 per well for 30 minutes Then 20 µL B-ASF were added and incubated for another 1 hour. To detect the signal, 5 µL (final conc. of 1.0 nM) terbium labelled Anti-His antibody was added and incubated for 30 min followed by adding 5 µL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in µM).

Gal-3 ELISA Assay

Materials:
1. Coating Buffer: Phosphate Buffered Saline (1×)—PBS
The Solution was prepared by dissolving the PBS packets procured from Sigma Aldrich (Catalogue No.: P3813-5× 10Pak) —1 Pack in 1 Liter of Milli-Q water.
2. Asialofetuin from fetal Calf Serum, Type-II. Sigma Aldrich (Catalogue No.: A1908-50MG).
3. Fetal Bovine Serum. Invitrogen (Catalogue No.: 26400-044-500 mL).
4. Tween-20. Sigma Aldrich (Catalogue No.: P1379-250 mL).
5. BD OptEIA Enzyme Reagent Streptavidin-HRP (Catalogue No.: 554066).
6. Sulphuric Acid. Sigma Aldrich (Catalogue No.: 25,810-5).
7. Paraformaldehyde. Sigma Aldrich (Catalogue No.: P6148-500G).
8. TMB Substrate. BD Biosciences (Catalogue No.: 555214).
9. Biotin-tagged hGalectin-3—A 0.82 mg/mL stock solution (28.6 kDa, 28.6713 µM) of biotin tagged hGal-3 in-house synthesized by the proteomic group was used for the titration.
10. TD-139 (EXT-001109-01-001): A small molecule synthesized in-house, used as an internal standard for the small molecule screening in hGalectin-3 neutralization binding assay.

A. Protocol
a. Coating of Plate: The ASF at concentration 15 nM was prepared in 1×PBS and was plated in the 96 well flat-bottom nunc plates (Nunc immuno plate, Maxisorp, Catalogue No.: 439454) according to the plate-map and was incubated overnight at 4° C. after sealing the plates with a top-seal.
b. Fixing and Blocking of Plate: On the assay day, the coating solution was drained and the plates were fixed by addition of 100 µL of 2% Paraformaldehyde solution and incubating at 37° C. for 30 min. and washed with 300 µL of wash buffer (PBS with 0.05% Tween-20) for 3 times, spin dried and taken for blocking.

The plates were later blocked with 10% FBS and incubated for 1 h at room temperature. Later the plate was washed with 3004, of wash buffer (PBS with 0.05% Tween-20) for 3 times.
B. Incubation: After spin drying the plates from previous washing, 1004, of test compounds, at various concentrations as specified in the plate-map (pre-incubated with the hGalectin-3 or mGalectin-3 at concentration 15 nM for 1 h at Room Temperature-RT) were added onto the plate as per the plate map. The plates were run in duplicates for data duplication and reproducibility.

These plates were incubated at RT for 1 h and were washed for 5 times with wash buffer, spin dried and 100 µL of Streptavidin HRP (1:1000 dilutions) was added and incubated for 1 h at room temperature and washed for 7 times with wash buffer.
C. Detection: After spin drying the plate from previous washing, 100 µL of TMB Substrate was added to each well and incubated for 15 min. at room temperature. Later the reaction was stopped with 2N sulphuric acid and the plate was read in spectramax at 450 nm Results: The read out (OD) obtained were plotted against the control wells after normalization with averaged controls and analyzed for the Log of Inhibitory concentration 50 (Log $IC_{50}$) values for program compounds.

Summary: The $IC_{50}$ values of the program compounds were as presented in the report (attached in excel format from Curve master compilation). The Plate control TD-139 had an $IC_{50}$ value of 10.3 nM and 108.12 nM for human and mouse Galectin-3 respectively. The same was plotted on the semilog graph.

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (MS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of the present invention to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

Section A

LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile:water with 0.1% TFA; Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in experimental procedures.

Methods of Preparation

Example 1 (Method A Representative)

(2R,3R,4S,5R,6R)-5-hydroxy-6-(hydroxymethyl)-3-methoxy-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide

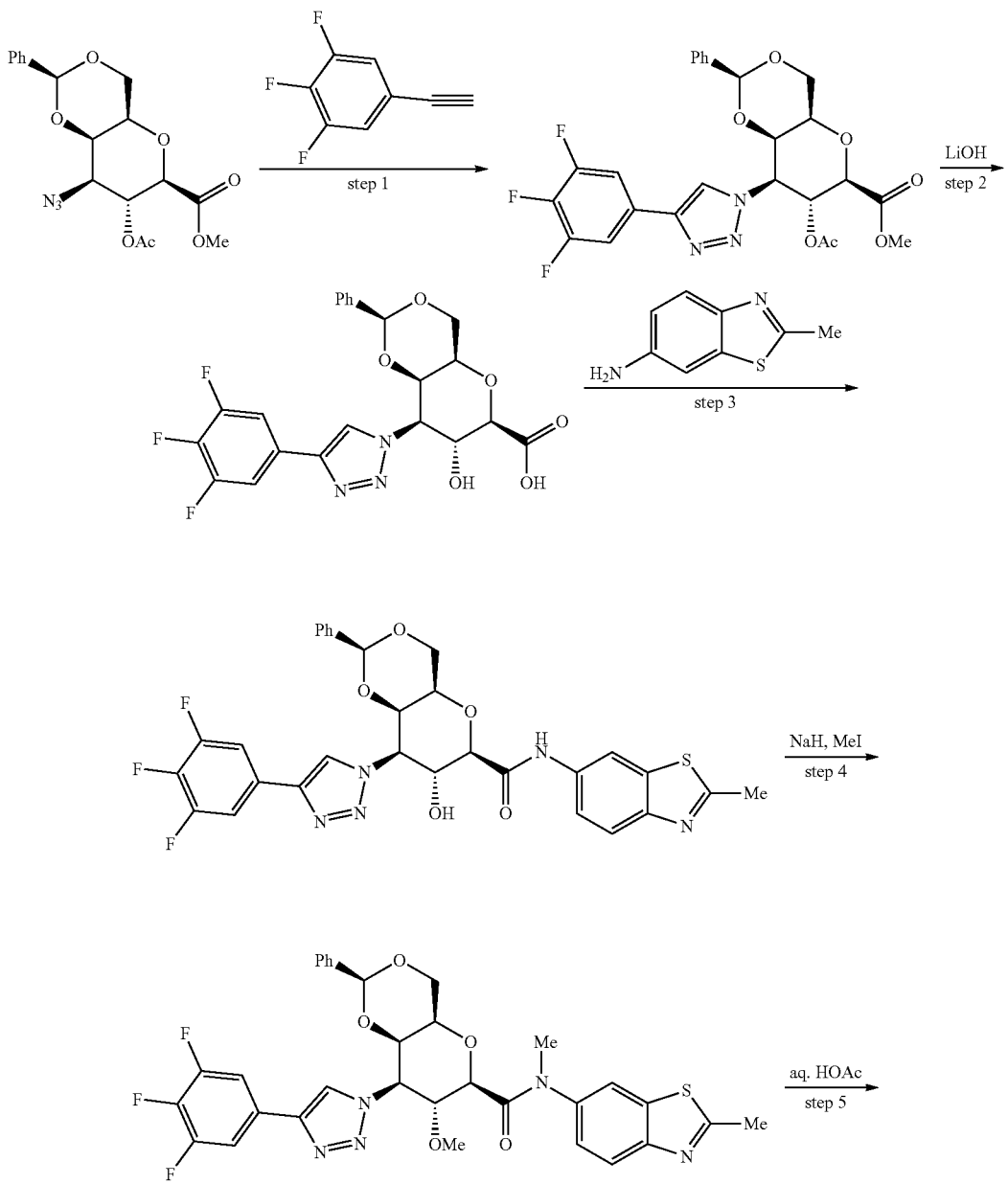

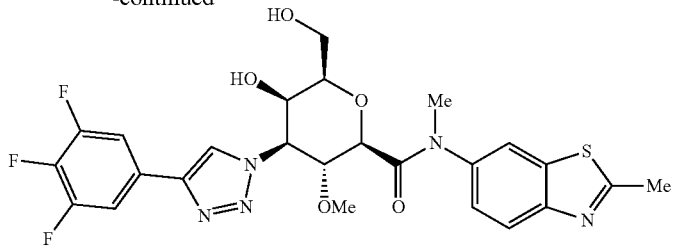

Example 1

Step 1. Methyl (2S,4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate To a solution of methyl (4aR,6R,7R,8S,8aR)-7-acetoxy-8-azido-2-phenylhexahydropyrano[3,2-d][1,3]dioxine-6-carboxylate (2.30 g, 6.10 mmol) in DMF (20.73 ml) and water (4.15 ml) were added sodium ascorbate (1.207 g, 6.10 mmol), copper(II) sulfate pentahydrate (1.370 g, 5.49 mmol), and 5-ethynyl-1,2,3-trifluorobenzene (1.713 g, 10.97 mmol). The reaction mixture was degassed and then heated at 85° C. for 1.5 h. The reaction mixture was poured into ice and filtered. The filter cake was washed with water (50 ml) and DCM (30 ml), and dried under vacuum to provide methyl (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate (3.4 g, 6.05 mmol, 99% yield) as a light yellow solid. LCMS (M+H)$^+$=534.0. $^1$H NMR (500 MHz, DMSO-d6) δ 8.83 (br s, 1H), 7.83 (br s, 2H), 7.46-7.31 (m, 5H), 5.69 (br s, 2H), 5.65-5.57 (m, 1H), 4.59 (br s, 1H), 4.53-4.45 (m, 1H), 4.17 (br d, J=14.0 Hz, 2H), 4.03 (br s, 1H), 3.66 (br s, 3H), 1.84 (br s, 3H).

Step 2. (2S,4aR,6R,7R,8R,8aR)-7-Hydroxy-2-phenyl-8-(4-(3,4,5-trifluorophenyl)-1H-1,2,3-triazol-1-yl)hexahydropyrano[3,2-d][1,3]dioxine-6-carboxylic Acid To a solution of methyl (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate (356 mg, 0.667 mmol) in THF (20 mL) at rt was added a solution of lithium hydroxide (80 mg, 3.34 mmol) in water (4 mL) over 2 min. The mixture was stirred at rt for 2.5 h. The reaction was complete and clean. The reaction mixture was concentrated under vacuum to dryness. To the residue was added water (4 mL) and the resulting mixture was acidified to pH 3-4 with 1 N HCl. The insoluble product, (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (0.320 g, 0.670 mmol, 100% yield), was collected as a beige solid by suction filtration and dried over Drierite under vacuum. LCMS (M+H)$^+$=478.0.

Step 3. (2S,4aR,6R,7R,8R,8aR)-7-hydroxy-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide A mixture of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (200 mg, 0.419 mmol), 2-methylbenzo[d]thiazol-6-amine (55 mg, 0.335 mmol), benzotriazol-1-yloxytris(dimethylamino)-phosphoniumhexafluorophosphate (BOP) (296 mg, 0.670 mmol), and N,N-diisopropylethylamine (0.190 mL, 1.089 mmol) in DMF (3.5 mL) was stirred at rt for 16 h. To the mixture was added water (10 mL), and the precipitating material was collected by suction filtration. The filter cake was further purified by flash chromatography (40 g silica gel, solid loading, 1-10% methanol/dichloromethane) to provide (4aR,6R,7R,8R,8aR)-7-hydroxy-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (96 mg, 0.154 mmol, 36.7% yield) as a beige solid. LCMS (M+H)$^+$=624.1.

Step 4. (2S,4aR,6R,7R,8R,8aR)-7-Methoxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide To a solution of (4aR,6R,7R,8R,8aR)-7-hydroxy-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (19 mg, 0.030 mmol) and iodomethane (2 N in t-butyl ethyl ether) (0.061 mL, 0.122 mmol) at 0° C. was added sodium hydride (60% oil dispersion) (4.87 mg, 0.122 mmol) in one portion. The mixture was stirred at rt for 30 min and then quenched with AcOH (0.5 mL). The mixture was diluted with acetic acid (0.5 mL) and injected to prep HPLC. The correct fraction was concentrated under vacuum, basified with saturated NaHCO$_3$ solution, and extracted with dichloromethane (3×20 mL). The combined extract was dried over anhydrous Na$_2$SO$_4$. Removal of the solvent under vacuum provided the desired product, (4aR,6R,7R,8R,8aR)-7-methoxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (9 mg, 0.014 mmol, 45.3% yield), as a white solid. $^1$H NMR (600 MHz, chloroform-d) δ 8.08 (s, 1H), 8.00 (d, J=8.5 Hz, 1H), 7.83 (br s, 1H), 7.48-7.37 (m, 8H), 5.44 (s, 1H), 4.80 (dd, J=10.6, 3.4 Hz, 1H), 4.42 (dd, J=10.6, 8.9 Hz, 1H), 4.29 (dd, J=12.6, 1.2 Hz, 1H), 4.22 (d, J=2.8 Hz, 1H), 3.95 (dd, J=12.5, 1.7 Hz, 1H), 3.79 (d, J=8.9 Hz, 1H), 3.40 (s, 3H), 3.11 (br s, 1H), 3.08 (s, 3H), 2.90 (s, 3H).

Step 5. (2R,3R,4S,5R,6R)-5-hydroxy-6-(hydroxymethyl)-3-methoxy-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide A solution of (4aR,6R,7R,8R,8aR)-7-methoxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (9 mg, 0.014 mmol) in 70% aq. acetic acid (1 mL) was heated at 70° C. for 4 h. The mixture was diluted with methanol (1 mL) and injected to prep. HPLC (Column: Phenomenex Luna AXIA 5 u C18 21.2× 100; Solvent A: 90% $H_2O$-10% methanol-0.1% TFA, Solvent B: 10% methanol-90% $H_2O$ 0.1% TFA; Start % B: 25, Final % B: 100). The correct fraction was concentrated under vacuum, basified with saturated $NaHCO_3$ solution, and extracted with dichloromethane (3×25 mL). The combined extract was dried over anhydrous $Na_2SO_4$. Removal of the solvent under vacuum provided the desired product, (2R,3R,4S,5R,6R)-5-hydroxy-6-(hydroxymethyl)-3-methoxy-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide (6.0 mg, 10.65 µmol, 77% yield), as a white solid. LCMS (M+H)$^+$=564.0. $^1$H NMR (500 MHz, methanol-d4) δ 8.69 (s, 1H), 8.10 (d, J=1.4 Hz, 1H), 8.00 (d, J=8.5 Hz, 1H), 7.68 (dd, J=8.8, 6.6 Hz, 2H), 7.56 (dd, J=8.5, 2.2 Hz, 1H), 4.69 (dd, J=10.7, 3.0 Hz, 1H), 4.50 (dd, J=10.7, 9.1 Hz, 1H), 3.93 (d, J=2.5 Hz, 1H), 3.81 (d, J=8.8 Hz, 1H), 3.77 (dd, J=11.7, 7.3 Hz, 1H), 3.64 (dd, J=11.7, 4.5 Hz, 1H), 3.43 (s, 3H), 3.36-3.34 (m, 1H), 3.15 (s, 3H), 2.89 (s, 3H). hGal-3 (HTRF) IC$_{50}$=0.087 µM.

Example 2 (Method B Representative)

(2R,3R,4S,5R,6R)-3,5-Dihydroxy-6-(hydroxymethyl)-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide

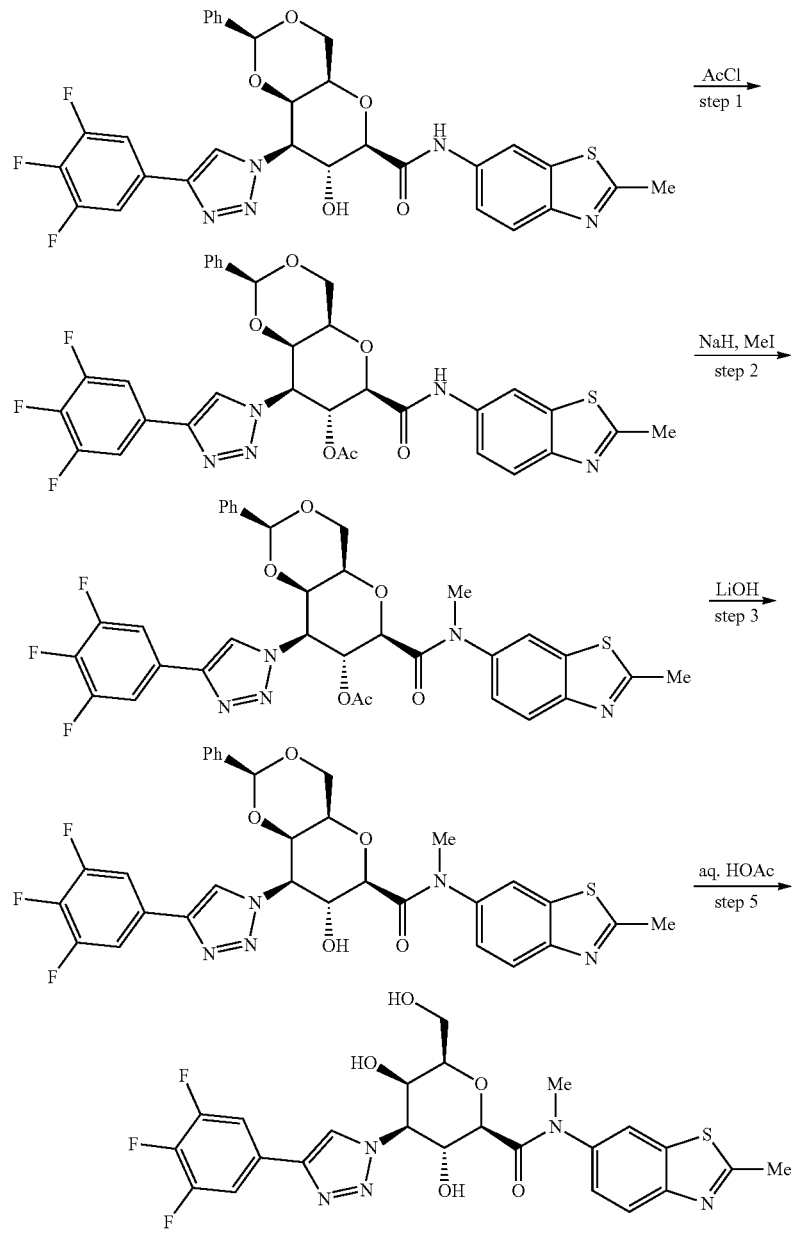

Example 2

Step 1. (2S,4aR,6R,7R,8S,8aR)-6-((2-Methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate To a solution of (4aR,6R,7R,8R,8aR)-7-hydroxy-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (70 mg, 0.112 mmol) in dichloromethane (5 mL) at 0° C. was added acetyl chloride (0.016 mL, 0.225 mmol), followed by pyridine (0.023 mL, 0.281 mmol). The mixture was stirred at rt for 30 min, diluted with ethyl acetate (60 mL), washed with water (15 mL), saturated NaHCO$_3$ solution (15 mL), and brine (15 mL). The organic layer was dried over MgSO$_4$. Removal of the solvent under vacuum provided the desired product, (4aR,6R,7R,8S,8aR)-6-((2-methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate (75 mg, 0.113 mmol, 100% yield), as a beige solid. LCMS (M+H)$^+$=666.1.

Step 2. (2S,4aR,6R,7R,8S,8aR)-6-(Methyl(2-methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate To a solution of (4aR,6R,7R,8S,8aR)-6-((2-methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate (75 mg, 0.113 mmol) and iodomethane (2 N in t-butyl ethyl ether) (0.085 mL, 0.169 mmol) at 0° C. was added sodium hydride (60% oil dispersion) (9.01 mg, 0.225 mmol) in one portion. The mixture was stirred at rt for 30 min and then quenched with AcOH (0.5 mL). The mixture was diluted with ethyl acetate (50 mL), washed with water (2×15 mL) and brine (15 mL), and dried over anhydrous Na$_2$SO$_4$. The desired product, (4aR,6R,7R,8S,8aR)-6-(methyl(2-methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate (50 mg, 0.074 mmol, 65.3% yield), was isolated as a white solid by flash chromatography (24 g silica gel, solid loading, 80-100% ethyl acetate/hexane). LCMS (M+H)$^+$=680.1.

Step 3. (2S,4aR,6R,7R,8R,8aR)-7-Hydroxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide To a solution of (4aR,6R,7R,8S,8aR)-6-(methyl(2-methylbenzo[d]thiazol-6-yl)carbamoyl)-2-phenyl-8-(4-(3,4,5-trifluorophenyl)-1H-1,2,3-triazol-1-yl)hexahydropyrano[3,2-d][1,3]dioxin-7-yl acetate (50 mg, 0.074 mmol) in THF (2.5 mL) at rt was added a solution of lithium hydroxide (8.81 mg, 0.368 mmol) in water (0.5 mL) over 2 min. The mixture was stirred at rt for 2 h, and then concentrated under vacuum to dryness. To the residue was added water (20 mL) and the resulting mixture was acidified to pH 3-4 with 2 N HCl. The insoluble product, (4aR,6R,7R,8R,8aR)-7-hydroxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (43 mg, 0.067 mmol, 92% yield), was collected as a beige solid by suction filtration and dried at 50° C. under vacuum. LCMS (M+H)$^+$=638.0.

Step 4. (2R,3R,4S,5R,6R)-3,5-Dihydroxy-6-(hydroxymethyl)-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide A solution of (4aR,6R,7R,8R,8aR)-7-hydroxy-N-methyl-N-(2-methylbenzo[d]thiazol-6-yl)-2-phenyl-8-(4-(3,4,5-trifluorophenyl)-1H-1,2,3-triazol-1-yl)hexahydropyrano[3,2-d][1,3]dioxine-6-carboxamide (43 mg, 0.067 mmol) in 70% aq. acetic acid (2 mL) was heated at 70° C. for 5 h. The mixture was diluted with methanol and injected to prep. HPLC (Column: Phenomenex Luna AXIA 5 u C18 21.2× 100; Solvent A: 90% H$_2$O-10% methanol-0.1% TFA, Solvent B: 10% methanol-90% H$_2$O 0.1% TFA; Start % B: 20, Final % B: 100). The correct fractions were concentrated under vacuum, basified with saturated NaHCO$_3$ solution, and extracted with dichloromethane (3×25 mL). The combined extract was dried over anhydrous Na$_2$SO$_4$. Removal of the solvent under vacuum provided the desired product, (2R,3R,4S,5R,6R)-3,5-dihydroxy-6-(hydroxymethyl)-N-methyl-N-(2-methylbenzo[d]thiazol-6-yl)-4-(4-(3,4,5-trifluorophenyl)-1H-1,2,3-triazol-1-yl)tetrahydro-2H-pyran-2-carboxamide (20 mg, 0.036 mmol, 54.0% yield), as a white solid. LCMS (M+H)$^+$=550.0. $^1$H NMR (500 MHz, methanol-d4) δ 8.54 (s, 1H), 8.10 (d, J=1.7 Hz, 1H), 8.00 (d, J=8.5 Hz, 1H), 7.65 (dd, J=8.7, 6.7 Hz, 2H), 7.57 (dd, J=8.5, 2.2 Hz, 1H), 4.76 (dd, J=11.0, 9.1 Hz, 1H), 4.64 (dd, J=11.0, 3.0 Hz, 1H), 3.97 (d, J=2.5 Hz, 1H), 3.84 (d, J=9.1 Hz, 1H), 3.75 (dd, J=11.6, 7.2 Hz, 1H), 3.68-3.61 (m, 1H), 3.42 (s, 3H), 3.38-3.34 (m, 1H), 2.89 (s, 3H). hGal-3 (HTRF) IC$_{50}$=0.109 μM.

Example 3 (Method C Representative)

(2R,3R,4S,5R,6R)—N-(6-chloroquinolin-8-yl)-5-hydroxy-6-(hydroxymethyl)-3-methoxy-N-methyl-4-(4-(3,4,5-trifluorophenyl)-1H-1,2,3-triazol-1-yl)tetrahydro-2H-pyran-2-carboxamide

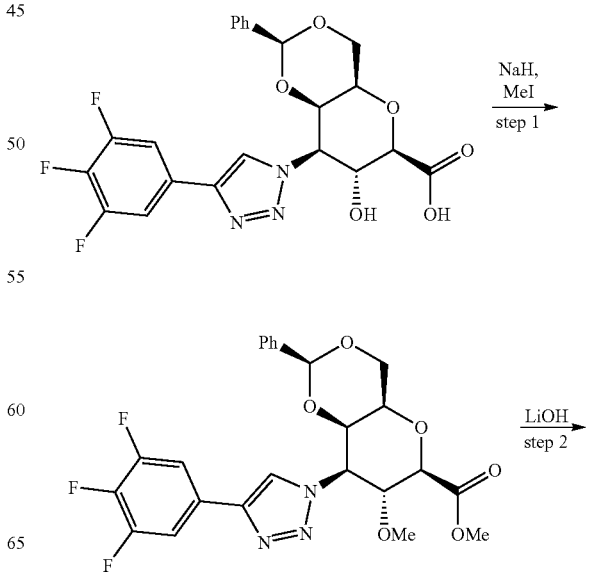

-continued

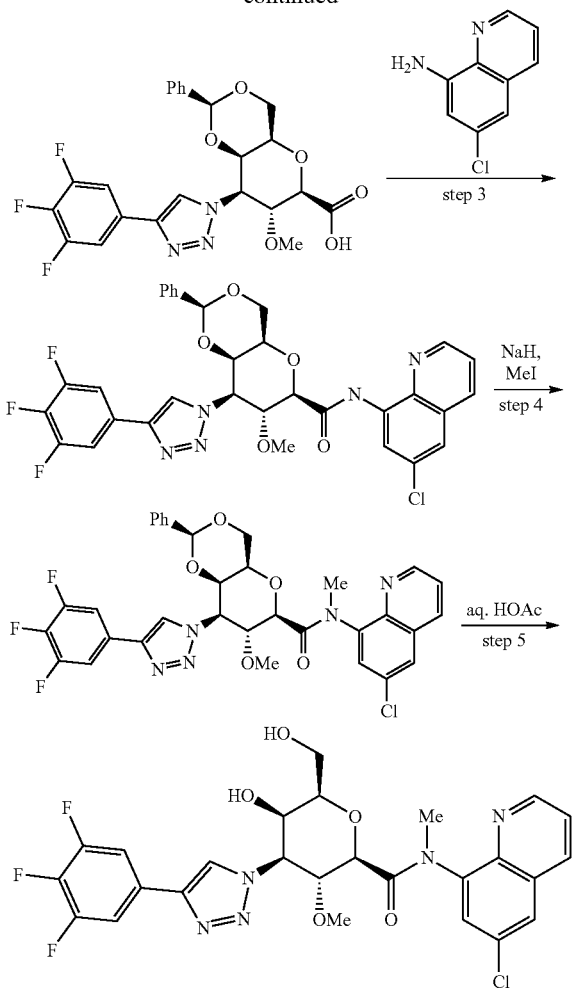

Example 3

Step 1. Methyl (2S,4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate To a solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (670 mg, 1.403 mmol) and iodomethane (0.349 mL, 5.61 mmol) in DMF (12 mL) at 0° C. was added sodium hydride (60% oil dispersion) (281 mg, 7.02 mmol) in one portion. The mixture was stirred at rt for 6 h and then at 50° C. for 10 h. It was re-cooled at 0° C. before additional iodomethane (0.175 mL, 2.80 mmol) and sodium hydride (60% oil dispersion) (140 mg, 2.31 mmol) were added. The mixture was heated at 50° C. for another 4 h. The mixture was cooled to 0° C. and quenched with acetic acid (1 mL, 17.47 mmol), diluted with water (150 mL), and adjusted its pH value to 7. The insoluble material was collected by suction filtration, followed by flash chromatography purification (80 g silica gel, solid loading, 30-65% ethyl acetate/hexane) to provide the desired product, methyl (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate (236 mg, 0.467 mmol, 33.3% yield), as a white solid. LCMS (M+H)$^+$=506.0.

Step 2. (2S,4aR,6R,7R,8R,8aR)-7-Methoxy-2-phenyl-8-(4-(3,4,5-trifluorophenyl)-1H-1,2,3-triazol-1-yl)hexahydropyrano[3,2-d][1,3]dioxine-6-carboxylic Acid To a solution of methyl (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate (234 mg, 0.463 mmol) in THF (10 mL) at rt was added a solution of lithium hydroxide (55.4 mg, 2.315 mmol) in water (2 mL) over 2 min. The mixture was stirred at rt for 2 h, and then concentrated under vacuum to dryness. To the residue was added water (10 mL) and the resulting mixture was acidified to pH 4-5 with 1 N HCl. The insoluble product, (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylic acid (221 mg, 0.450 mmol, 97% yield), was collected as a white solid by suction filtration and dried at 50° C. under vacuum. LCMS (M+H)$^+$=492.0.

Step 3. (2S,4aR,6R,7R,8R,8aR)—N-(6-Chloroquinolin-8-yl)-7-methoxy-2-phenyl-8-(4-(3,4,5-trifluorophenyl)-1H-1,2,3-triazol-1-yl)hexahydropyrano[3,2-d][1,3]dioxine-6-carboxamide A mixture of (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylic acid (25 mg, 0.051 mmol), 6-chloroquinolin-8-amine (18.17 mg, 0.102 mmol), benzotriazol-1-yloxytris(dimethylamino)-phosphoniumhexafluorophosphate (BOP) (36.0 mg, 0.081 mmol), and N,N-diisopropylethylamine (0.036 mL, 0.203 mmol) in DMF (0.5 mL) was stirred at rt for 7 h. The mixture was diluted with methanol and injected to prep. HPLC (Column: Phenomenex Luna AXIA 5 u C18 21.2×100; Solvent A: 90% H$_2$O-10% methanol-0.1% TFA, Solvent B: 10% methanol-90% H$_2$O 0.1% TFA; Start % B: 44, Final % B: 100). The corrected fractions were combined, concentrated under vacuum, basified with saturated NaHCO$_3$ solution, and extracted with dichloromethane (3×25 mL). The combined extract was dried over anhydrous Na$_2$SO$_4$. Removal of the solvent under vacuum provided the desired product, (4aR,6R,7R,8R,8aR)—N-(6-chloroquinolin-8-yl)-7-methoxy-2-phenyl-8-(4-(3,4,5-trifluorophenyl)-1H-1,2,3-triazol-1-yl)hexahydropyrano[3,2-d][1,3]dioxine-6-carboxamide (12 mg, 0.018 mmol, 36.2% yield), as a beige solid. LCMS (M+H)$^+$=652.0.

Step 4. (2S,4aR,6R,7R,8R,8aR)—N-(6-Chloroquinolin-8-yl)-7-methoxy-N-methyl-2-phenyl-8-(4-(3,4,5-trifluorophenyl)-1H-1,2,3-triazol-1-yl)hexahydropyrano[3,2-d][1,3]dioxine-6-carboxamide To a solution of (4aR,6R,7R,8R,8aR)—N-(6-chloroquinolin-8-yl)-7-methoxy-2-phenyl-8-(4-(3,4,5-trifluorophenyl)-1H-1,2,3-triazol-1-yl)hexahydropyrano[3,2-d][1,3]dioxine-6-carboxamide (12 mg, 0.018 mmol) and iodomethane (2 N in t-butyl ethyl ether) (0.023 mL, 0.046 mmol) in at 0° C. was added sodium hydride (60% oil dispersion) (1.840 mg, 0.046 mmol) in one portion. The mixture was stirred at rt for 30 min, and then quenched with AcOH (0.5 mL). The mixture was diluted with ethyl acetate (50 mL), washed with saturated NaHCO$_3$ solution (15 mL), water (2×15 mL), an brine (15 mL). The organic layer was dried over anhydrous MgSO$_4$ and concentrated under vacuum to provide (4aR,6R,7R,8R,8aR)—N-(6-chloroquinolin-8-yl)-7-methoxy-N-methyl-2-phenyl-8-(4-(3,4,5-trifluorophenyl)-1H-1,2,3-triazol-1-yl)hexahydropyrano[3,2-d][1,3]dioxine-6-carboxamide (12 mg, 0.018 mmol, 98% yield) as a beige solid. LCMS (M+H)$^+$=666.1.

Step 5. (2R,3R,4S,5R,6R)—N-(6-chloroquinolin-8-yl)-5-hydroxy-6-(hydroxymethyl)-3-methoxy-N-methyl-4-(4-(3,4,5-trifluorophenyl)-1H-1,2,3-triazol-1-yl)tetrahydro-2H-pyran-2-carboxamide A solution of (4aR,6R,7R,8R,8aR)—N-(6-chloroquinolin-8-yl)-7-methoxy-N-methyl-2-phenyl-8-(4-(3,4,5-trifluorophenyl)-1H-1,2,3-triazol-1-yl)hexahydropyrano[3,2-d][1,3]dioxine-6-carboxamide (12 mg, 0.018 mmol) in 70% acetic acid (1 mL) was heated at 70° C. for 6 h. The mixture was diluted with methanol and injected to prep. HPLC (Column: Phenomenex Luna AXIA 5 u C18 21.2×100; Solvent A: 90% H$_2$O-10% methanol-0.1% TFA, Solvent B: 10% methanol-90% H$_2$O 0.1% TFA; Start % B: 25, Final % B: 100). The correct fractions were combined, concentrated under vacuum, basified with 1 N K$_2$HPO$_4$ solution, and extracted with dichloromethane (3×25 mL). The combined extract was dried over anhydrous Na$_2$SO$_4$. Removal of the solvent under vacuum provided (2R,3R,4S,5R,6R)—N-(6-chloroquinolin-8-yl)-5-hydroxy-6-(hydroxymethyl)-3-methoxy-N-methyl-4-(4-(3,4,5-trifluorophenyl)-1H-1,2,3-triazol-1-yl)tetrahydro-2H-pyran-2-carboxamide (4.0 mg, 6.48 μmol, 36.0% yield) as a white solid. LCMS (M+H)$^+$=578.0. $^1$H NMR (500 MHz, METHANOL-d4) δ 9.02-8.93 (m, 1H), 8.66 (s, 1H), 8.46-8.36 (m, 1H), 8.14 (br d, J=2.2 Hz, 1H), 8.03 (br s, 1H), 7.73-7.61 (m, 3H), 4.61-4.55 (m, 1H), 4.56-4.49 (m, 1H), 3.93 (br s, 1H), 3.82-3.74 (m, 1H), 3.72-3.64 (m, 1H), 3.48 (s, 3H), 3.44-3.39 (m, 1H), 3.30-3.26 (m, 1H), 3.21-3.13 (s, 3H). hGal-3 (HTRF) IC$_{50}$=0.057 μM.

Example 4 (Method D Representative)

(2R,3R,4S,5R,6R)—N-(Benzo[d]thiazol-6-yl)-4-(4-(4-chloro-3,5-difluorophenyl)-1H-1,2,3-triazol-1-yl)-5-hydroxy-6-(hydroxymethyl)-3-methoxy-N-methyltetrahydro-2H-pyran-2-carboxamide

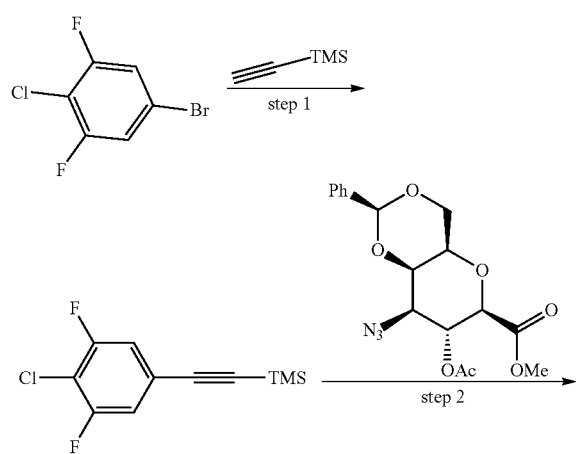

Example 4

Step 1. ((4-Chloro-3,5-difluorophenyl)ethynyl)trimethylsilane

To a degassed mixture of 5-bromo-2-chloro-1,3-difluorobenzene (27.3 g, 120 mmol), copper(I) iodide (0.389 g, 2.041 mmol) and bis(triphenylphosphine)palladium(II) chloride (1.432 g, 2.041 mmol) in triethylamine (120 ml) at rt was added ethynyltrimethylsilane (17.30 ml, 122 mmol) dropwise under nitrogen over 20 min. The mixture was stirred at rt until the reaction was complete (monitored by HPLC). It was diluted with hexanes (100 mL) and insoluble material was removed by filtration. The filtrate was concentrated under vacuum and the residue was loaded onto a 220 g silica gel flash column, eluting with hexanes to afford ((4-chloro-3,5-difluorophenyl)ethynyl)trimethylsilane (29.23 g, 109 mmol, 91% yield) as an oil. $^1$H NMR (400 MHz, chloroform-d) δ 7.03-7.10 (m, 2H), 0.22-0.29 (m, 9H).

Step 2. Methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate To a solution of methyl (4aR,6R,7R,8S,8aR)-7-acetoxy-8-azido-2-phenylhexahydropyrano[3,2-d][1,3]dioxine-6-carboxylate (0.200 g, 0.530 mmol) in DMF (3.79 ml) and water (1.514 ml) were added (+)-sodium-ascorbate (0.105 g, 0.530 mmol), copper(II) sulfate pentahydrate (0.119 g, 0.477 mmol), and ((4-chloro-3,5-difluorophenyl)ethynyl)trimethylsilane (0.259 g, 1.060 mmol). The reaction mixture was degassed and heated at 85° C. for 1.5 h. The reaction was poured into ice. The resulting insoluble material was collected by suction filtration and dried under vacuum. The crude product was further purified with flash chromatography (24 g silica gel, solid loading, 0-50% ethyl acetate/dichloromethane) to provide methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (286 mg, 0.520 mmol, 98% yield) as a white solid. LCMS (M+H)$^+$=550.1. $^1$H NMR (400 MHz, chloroform-d) δ 8.08 (s, 1H), 7.42-7.46 (m, 5H), 7.39-7.41 (m, 1H), 7.37-7.39 (m, 1H), 5.88 (dd, J=9.46, 11.00 Hz, 1H), 5.52 (s, 1H), 5.20 (dd, J=3.41, 10.89 Hz, 1H), 4.45-4.51 (m, 2H), 4.23 (d, J=9.68 Hz, 1H), 4.09-4.16 (m, 1H), 3.81 (s, 3H), 3.79 (d, J=1.10 Hz, 1H), 1.88 (s, 3H).

Step 3. (4aR,6R,7R,8R,8aR)-8-(4-(4-Chloro-3,5-difluorophenyl)-1H-1,2,3-triazol-1-yl)-7-hydroxy-2-phenylhexahydropyrano[3,2-d][1,3]dioxine-6-carboxylic acid To a solution of methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (286 mg, 0.520 mmol) in THF (11.0 mL) was added LiOH (1N aq solution) (2.60 mL, 2.60 mmol). The reaction mixture was stirred at rt for 30 min, diluted with water (10 ml), acidified to pH 5 with 1N HCl aq solution, and extracted with ethyl acetate (2×20 ml). The combined extract was dried over MgSO$_4$, filtered and concentrated under vacuum to provide (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxylic acid (241 mg, 0.488 mmol, 94% yield) as a white solid. LCMS (M+H)$^+$=494.1. $^1$H NMR (400 MHz, DMSO-d6) δ 8.93 (s, 1H), 7.84 (d, J=8.36 Hz, 2H), 7.29-7.36 (m, 5H), 5.52 (s, 1H), 5.10 (td, J=3.52, 6.60 Hz, 1H), 4.43 (br s, 2H), 4.04-4.21 (m, 2H), 3.87 (br s, 2H).

Step 4. (4aR,6R,7R,8R,8aR)—N-(Benzo[d]thiazol-6-yl)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide To (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxylic acid (108 mg, 0.219 mmol) and benzo[d]thiazol-6-amine, 2 HCl (53.7 mg, 0.241 mmol) in dichloromethane (5 mL) was added N,N-diisopropylethylamine (0.153 mL, 0.875 mmol), followed by 2,4,6-tripropyl-1,3,5,2,4,6-trioxatriphosphinane 2,4,6-trioxide (50% solution in EtOAc) (557 mg, 0.875 mmol). The resulting solution was stirred at rt for 1 h and then concentrated under vacuum. The residue was subjected to flash chromatography (80 g silica gel, solid loading, 0-90% ethyl acetate/hexane) to provide (4aR,6R,7R,8R,8aR)—N-(benzo[d]thiazol-6-yl)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (106 mg, 0.169 mmol, 77% yield) as a white solid. LCMS (M+H)$^+$=626.2. $^1$H NMR (400 MHz, chloroform-d) δ 8.98 (s, 1H), 8.76 (s, 1H), 8.54 (d, J=2.20 Hz, 1H), 8.12 (d, J=8.80 Hz, 1H), 8.06-8.08 (m, 1H), 7.50 (dd, J=1.98, 8.80 Hz, 1H), 7.41-7.46 (m, 2H), 7.38 (s, 4H), 5.55 (s, 1H), 5.14 (dd, J=3.08, 10.56 Hz, 1H), 4.98 (br s, 1H), 4.69 (t, J=10.01 Hz, 1H), 4.63 (d, J=2.64 Hz, 1H), 4.56 (dd, J=1.21, 12.87 Hz, 1H), 4.23 (d, J=9.46 Hz, 2H), 3.95 (s, 1H).

Step 5. (4aR,6R,7R,8R,8aR)—N-(Benzo[d]thiazol-6-yl)-8-(4-(4-chloro-3,5-difluorophenyl)-1H-1,2,3-triazol-1-yl)-7-methoxy-N-methyl-2-phenylhexahydropyrano[3,2-d][1,3]dioxine-6-carboxamide To (4aR,6R,7R,8R,8aR)—N-(benzo[d]thiazol-6-yl)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (25 mg, 0.040 mmol) in DMF (1.0 mL) was added sodium hydride (60% oil dispersion) (7.99 mg, 0.200 mmol), followed by iodomethane (0.012 mL, 0.200 mmol). The resulting mixture was stirred at rt for 30 min, quenched with water (10 mL), and extracted with ethylacetate (20 mL). The organic solution was dried over MgSO$_4$ and concentrated under vacuum. The residue was subjected to flash chromatography (12 g silica gel, 0-90% ethyl acetate/hexane) to provide (4aR,6R,7R,8R,8aR)—N-(benzo[d]thiazol-6-yl)-8-(4-(4-chloro-3,5-difluorophenyl)-1H-1,2,3-triazol-1-yl)-7-methoxy-N-methyl-2-phenylhexahydropyrano[3,2-d][1,3]dioxine-6-carboxamide (22 mg, 0.034 mmol, 84% yield) as a beige solid. LCMS (M+H)$^+$=654.2. $^1$H NMR (400 MHz, CHLOROFORM-d) δ 8.21 (d, J=8.58 Hz, 1H), 8.13 (s, 1H), 7.96-8.06 (m, 2H), 7.54 (dd, J=1.98, 8.58 Hz, 1H), 7.38-7.48 (m, 7H), 5.44 (s, 1H), 4.81 (dd, J=3.30, 10.56 Hz, 1H), 4.43 (dd, J=9.02, 10.56 Hz, 1H), 4.30 (dd, J=1.21, 12.65 Hz, 1H), 4.19-4.25 (m, 1H), 3.95 (dd, J=1.54, 12.76 Hz, 1H), 3.80 (d, J=9.02 Hz, 1H), 3.42 (s, 3H), 3.12 (s, 1H), 3.08 (s, 3H).

Step 6. (2R,3R,4S,5R,6R)—N-(Benzo[d]thiazol-6-yl)-4-(4-(4-chloro-3,5-difluorophenyl)-1H-1,2,3-triazol-1-yl)-5-hydroxy-6-(hydroxymethyl)-3-methoxy-N-methyltetrahydro-2H-pyran-2-carboxamide A mixture of (4aR,6R,7R,8R,8aR)—N-(benzo[d]thiazol-6-yl)-8-(4-(4-chloro-3,5-difluorophenyl)-1H-1,2,3-triazol-1-yl)-7-methoxy-N-methyl-2-phenylhexahydropyrano[3,2-d][1,3]dioxine-6-carboxamide (22 mg, 0.034 mmol) in acetic acid (0.7 mL) and water (0.3 mL) was heated at 65° C. overnight. The reaction was diluted with methanol and injected to prep. HPLC (Column: Phenomenex Luna AXIA 5 u 30×100; Solvent A: 90% H$_2$O-10% ACN-0.1% TFA, Solvent B: 90% ACN-10% H$_2$O 0.1% TFA; Start % B: 25, Final % B: 80). The correct fractions were combined, concentrated under vacuum, basified with saturated NaHCO$_3$ solution, and extracted with dichloromethane (2×25 mL). Removal of the solvent under vacuum provided the desired product, (2R,3R,4S,5R,6R)—N-(benzo[d]thiazol-6-yl)-4-(4-(4-chloro-3,5-difluorophenyl)-1H-1,2,3-triazol-1-yl)-5-hydroxy-6-(hydroxymethyl)-3-methoxy-N-methyltetrahydro-2H-pyran-2-carboxamide (11 mg, 0.019 mmol, 56.6% yield), as a white solid. LCMS (M+H)$^+$=566.1. $^1$H NMR (400 MHz, methanol-d4) δ 9.35 (s, 1H), 8.73 (s, 1H), 8.22-8.27 (m, 1H), 8.12-8.22 (m, 1H), 7.64-7.70 (m, 2H), 7.58-7.64 (m, 1H), 4.69 (dd, J=2.86, 10.78 Hz, 1H), 4.50 (dd, J=9.13, 10.67 Hz, 1H), 3.91 (d, J=2.42 Hz, 1H), 3.78-3.83 (m, 1H), 3.73-3.78 (m, 1H), 3.63 (dd, J=4.51, 11.77 Hz, 1H), 3.43 (s, 3H), 3.34 (br s, 1H), 3.14 (s, 3H). hGal-3 (HTRF) $IC_{50}$=0.033 μM.

Example 5 (Method E Representative)

(2R,3R,4S,5R,6R)—N-(5-Chloro-2-(trifluoromethyl) phenyl)-4-(4-(4-chloro-3,5-difluorophenyl)-1H-1,2, 3-triazol-1-yl)-3,5-dihydroxy-6-(hydroxymethyl)-N-methyltetrahydro-2H-pyran-2-carboxamide

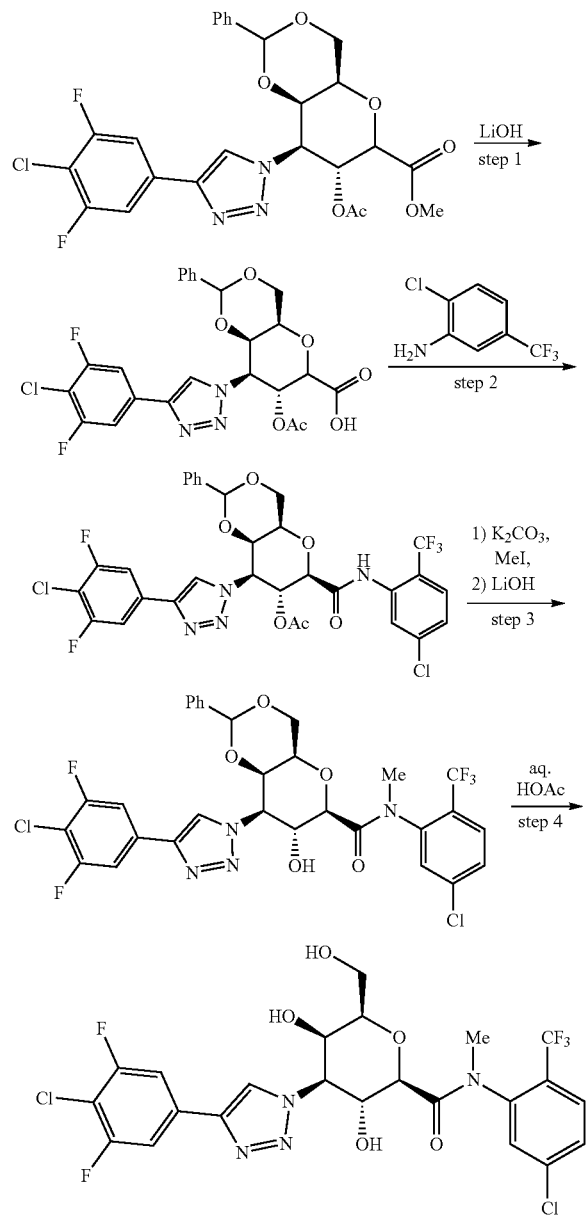

Example 5

Step 1. (4aR,6R,7R,8S,8aR)-7-Acetoxy-8-(4-(4-chloro-3,5-difluorophenyl)-1H-1,2,3-triazol-1-yl)-2-phenylhexahydropyrano[3,2-d][1,3]dioxine-6-carboxylic Acid To a suspension of methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (1.1 g, 2.000 mmol) in THF (45.5 ml) and methanol (4.55 ml) was added lithium hydroxide (1N aq solution) (2.000 ml, 2.000 mmol) dropwise. The reaction mixture was stirred at rt overnight, diluted with water (30 mL), acidified to pH 3-4 with 1M HCl aq solution, and extracted with EtOAc (2×50 mL). The combined extract was dried over $MgSO_4$, filtered and concentrated under vacuum. The residue was subjected to flash chromatography (80 g silica gel, solid loading, 0-15% methanol/dichloromethane) to provide (4aR,6R,7R,8S,8aR)-7-acetoxy-8-(4-(4-chloro-3,5-difluorophenyl)-1H-1,2,3-triazol-1-yl)-2-phenylhexahydropyrano [3,2-d][1,3]dioxine-6-carboxylic acid (215 mg, 0.401 mmol, 20% yield), as a white solid. LCMS $(M+H)^+$=536.2. $^1$H NMR (400 MHz, methanol-d4) δ 8.33 (s, 1H), 7.42-7.49 (m, 4H), 7.36-7.40 (m, 3H), 5.84 (t, J=10.23 Hz, 1H), 5.58 (s, 1H), 5.40 (dd, J=2.97, 10.89 Hz, 1H), 4.56 (d, J=3.08 Hz, 1H), 4.39 (d, J=12.76 Hz, 1H), 4.31 (d, J=9.68 Hz, 1H), 4.17 (d, J=12.76 Hz, 1H), 3.92 (s, 1H), 1.85 (s, 3H).

Step 2. (4aR,6R,7R,8S,8aR)-6-((5-Chloro-2-(trifluoromethyl)phenyl)carbamoyl)-8-(4-(4-chloro-3,5-difluorophenyl)-1H-1,2,3-triazol-1-yl)-2-phenylhexahydropyrano[3,2-d][1,3]dioxin-7-yl acetate To (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylic acid (66 mg, 0.123 mmol) and 5-chloro-2-(trifluoromethyl)aniline (27.7 mg, 0.142 mmol) in DCE (1.0 mL) was added pyridine (0.040 mL, 0.493 mmol), followed by 2,4,6-tripropyl-1,3,5,2,4,6-trioxatriphosphinane 2,4,6-trioxide (50% solution in EtOAc) (314 mg, 0.493 mmol). The resulting solution was stirred at 80° C. for 2 h. The mixture was concentrated under vacuum and the residue was subjected to flash chromatography (12 g silica gel, 0-5% methanol/dichloromethane) to provide (4aR,6R,7R,8S,8aR)-6-((5-chloro-2-(trifluoromethyl)phenyl)carbamoyl)-8-(4-(4-chloro-3,5-difluorophenyl)-1H-1,2, 3-triazol-1-yl)-2-phenylhexahydropyrano[3,2-d][1,3]dioxin-7-yl acetate (70 mg, 0.098 mmol, 80% yield) as a film. LCMS $(M+H)^+$=713.3. $^1$H NMR (400 MHz, chloroform-d) δ 9.06 (br s, 1H), 8.29 (d, J=1.32 Hz, 1H), 7.96 (s, 1H), 7.57 (d, J=8.58 Hz, 1H), 7.41-7.45 (m, 5H), 7.37 (d, J=7.48 Hz, 2H), 7.24 (dd, J=1.10, 8.36 Hz, 1H), 5.83 (dd, J=9.68, 11.00 Hz, 1H), 5.54 (s, 1H), 5.28-5.34 (m, 1H), 4.55 (d, J=3.08 Hz, 1H), 4.49 (dd, J=1.43, 12.87 Hz, 1H), 4.28 (d, J=9.68 Hz, 1H), 4.18 (dd, J=1.54, 12.98 Hz, 1H), 3.94 (d, J=0.66 Hz, 1H), 1.98 (s, 3H).

Step 3. (4aR,6R,7R,8R,8aR)—N-(5-Chloro-2-(trifluoromethyl)phenyl)-8-(4-(4-chloro-3,5-difluorophenyl)-1H-1,2,3-triazol-1-yl)-7-hydroxy-N-methyl-2-phenylhexahydropyrano[3,2-d][1,3]dioxine-6-carboxamide To (4aR,6R,7R,8S,8aR)-6-((5-chloro-2-(trifluoromethyl) phenyl)carbamoyl)-8-(4-(4-chloro-3,5-difluorophenyl)-1H-1,2,3-triazol-1-yl)-2-phenylhexahydropyrano[3,2-d][1,3]dioxin-7-yl acetate (35 mg, 0.037 mmol) and $K_2CO_3$ (25.4 mg, 0.184 mmol) in DMF (1.0 mL) was added iodomethane (6.87 μl, 0.110 mmol). The resulting mixture was stirred at 90° C. for 1 h and concentrated in vacuum to remove volatiles. To the remaining solution was added lithium hydroxide (1N aq solution) (0.110 mL, 0.110 mmol), and the mixture was stirred at rt for 30 min. The mixture was concentrated under vacuum to dryness and the residue was subjected to flash chromatography (12 g silica gel, 0-4% methanol/dichloromethane) to provide (4aR,6R,7R,8R, 8aR)—N-(5-chloro-2-(trifluoromethyl)phenyl)-8-(4-(4-chloro-3,5-difluorophenyl)-1H-1,2,3-triazol-1-yl)-7-hydroxy-N-methyl-2-phenylhexahydropyrano[3,2-d][1,3]dioxine-6-carboxamide (19 mg, 0.028 mmol, 75% yield), as a film. LCMS (M+H)$^+$=685.3.

Step 4. (2R,3R,4S,5R,6R)—N-(5-Chloro-2-(trifluoromethyl)phenyl)-4-(4-(4-chloro-3,5-difluorophenyl)-1H-1,2,3-triazol-1-yl)-3,5-dihydroxy-6-(hydroxymethyl)-N-methyltetrahydro-2H-pyran-2-carboxamide A mixture of (4aR,6R,7R,8R,8aR)—N-(5-chloro-2-(trifluoromethyl)phenyl)-8-(4-(4-chloro-3,5-difluorophenyl)-1H-1,2,3-triazol-1-yl)-7-hydroxy-N-methyl-2-phenylhexahydropyrano[3,2-d][1,3]dioxine-6-carboxamide (19 mg, 0.028 mmol) in acetic acid (0.7 mL) and water (0.3 mL) was stirred at 90° C. for 2 h. The mixture was diluted with methanol and injected to prep. HPLC (Column: Phenomenex Luna AXIA 30×100 mm C18 5 u; Solvent A: 90% H$_2$O-10% ACN-0.1% TFA, Solvent B: 90% ACN-10% H$_2$O 0.1% TFA; Start % B: 30, Final % B: 70). The correct fractions were combined, concentrated under vacuum, basified with saturated NaHCO$_3$ solution, and extracted with dichloromethane (2×25 mL). Removal of the solvent under vacuum provided the desired product, (2R,3R,4S,5R,6R)—N-(5-chloro-2-(trifluoromethyl)phenyl)-4-(4-(4-chloro-3,5-difluorophenyl)-1H-1,2,3-triazol-1-yl)-3,5-dihydroxy-6-(hydroxymethyl)-N-methyltetrahydro-2H-pyran-2-carboxamide (5 mg, 7.95 μmol, 28.7% yield) as an off-white solid. LCMS (M+H)$^+$=597.2; $^1$H NMR (400 MHz, methanol-d4) δ 8.57 (d, J=5.06 Hz, 1H), 7.86 (d, J=8.58 Hz, 1H), 7.79 (d, J=1.76 Hz, 1H), 7.68-7.74 (m, 1H), 7.65 (d, J=7.92 Hz, 2H), 7.56 (d, J=1.54 Hz, 1H), 4.68 (dd, J=2.75, 11.33 Hz, 1H), 4.47-4.65 (m, 1H), 4.01 (d, J=2.86 Hz, 1H), 3.80 (d, J=8.80 Hz, 1H), 3.66-3.72 (m, 1H), 3.60-3.65 (m, 1H), 3.50-3.53 (m, 1H), 3.27 (d, J=5.28 Hz, 3H). hGal-3 (HTRF) IC$_{50}$=0.051 μM.

Example 6 (Method F Representative)

(2R,3R,4S,5R,6R)—N-(Benzo[b]thiophen-6-yl)-3,5-dihydroxy-6-(hydroxymethyl)-N-methyl-4-(4-(3,4,5-trifluorophenyl)-1H-1,2,3-triazol-1-yl)tetrahydro-2H-pyran-2-carboxamide

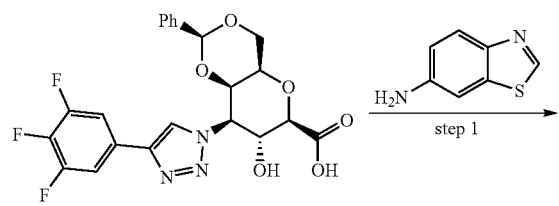

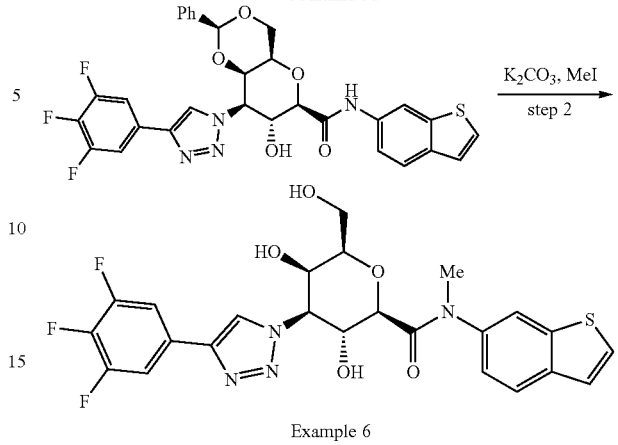

Example 6

Step 1. (4aR,6R,7R,8R,8aR)—N-(Benzo[b]thiophen-6-yl)-7-hydroxy-2-phenyl-8-(4-(3,4,5-trifluorophenyl)-1H-1,2,3-triazol-1-yl)hexahydropyrano[3,2-d][1,3]dioxine-6-carboxamide To (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (100 mg, 0.209 mmol) and benzo[b]thiophen-6-amine (34.4 mg, 0.230 mmol) in DCM (3.0 mL) was added N,N-diisopropylethylamine (0.146 mL, 0.838 mmol), followed by 2,4,6-tripropyl-1,3,5, 2,4,6-trioxatriphosphinane 2,4,6-trioxide (50% in EtOAc) (533 mg, 0.838 mmol). The resulting solution was stirred at rt for 1 h, concentrated under vacuum. The residue was subjected to flash chromatography purification (12 g silica gel, 0-3% methanol/dichloromethane) to provide (4aR,6R, 7R,8R,8aR)—N-(benzo[b]thiophen-6-yl)-7-hydroxy-2-phenyl-8-(4-(3,4,5-trifluorophenyl)-1H-1,2,3-triazol-1-yl)hexahydropyrano[3,2-d][1,3]dioxine-6-carboxamide (111 mg, 0.182 mmol, 87% yield) as an off-white solid. LCMS (M+H)$^+$=609.2; $^1$H NMR (400 MHz, chloroform-d) δ 8.66 (s, 1H), 8.36 (d, J=1.98 Hz, 1H), 8.03 (s, 1H), 7.81 (d, J=8.36 Hz, 1H), 7.40-7.46 (m, 4H), 7.38-7.39 (m, 4H), 7.32 (dd, J=0.66, 5.28 Hz, 1H), 5.54 (s, 1H), 5.09-5.17 (m, 1H), 5.05-5.09 (m, 1H), 4.65-4.74 (m, 1H), 4.51-4.63 (m, 2H), 4.22-4.25 (m, 1H), 4.17-4.22 (m, 1H), 3.90-3.96 (m, 1H).

Step 2. (2R,3R,4S,5R,6R)—N-(Benzo[b]thiophen-6-yl)-3,5-dihydroxy-6-(hydroxymethyl)-N-methyl-4-(4-(3,4,5-trifluorophenyl)-1H-1,2,3-triazol-1-yl)tetrahydro-2H-pyran-2-carboxamide To (4aR,6R,7R,8R,8aR)—N-(benzo[b]thiophen-6-yl)-7-hydroxy-2-phenyl-8-(4-(3,4,5-trifluorophenyl)-1H-1,2,3-triazol-1-yl)hexahydropyrano[3,2-d][1,3]dioxine-6-carboxamide (55 mg, 0.090 mmol) and K$_2$CO$_3$ (62.4 mg, 0.452 mmol) in DMF (2.0 mL) in a sealed tube was added iodomethane (38.5 mg, 0.271 mmol). The resulting mixture was stirred at 60° C. for 1 day and then at 90° C. for 2 day. The mixture was diluted with methanol and injected to prep. HPLC (Column: Phenomenex Luna AXIA 30×100 mm C18 5 u; Solvent A: 90% H$_2$O-10% ACN-0.1% TFA, Solvent B: 90% ACN-10% H$_2$O 0.1% TFA; Start % B: 30, Final % B: 60). The correct fractions were combined, concentrated under vacuum, basified with saturated NaHCO$_3$ solution, and extracted with dichloromethane (2×25 mL). Removal of the solvent under vacuum provided the desired product, (2R,3R,4S,5R,6R)—N-(benzo[b]thiophen-6-yl)-3,5-dihydroxy-6-(hydroxymethyl)-N-methyl-4-(4-(3,4,5-trifluorophenyl)-1H-1,2,3-triazol-1-yl)tetrahydro-2H-pyran-2-carboxamide (11 mg, 0.020 mmol, 21.63% yield), as a tan solid. LCMS (M+H)$^+$=535.1; $^1$H NMR (500 MHz, methanol-d4) δ 8.52 (s, 1H), 8.04 (s, 1H), 7.95 (d, J=8.25 Hz, 1H), 7.70 (d, J=5.50 Hz, 1H), 7.63 (dd, J=6.74, 8.67 Hz, 2H), 7.45 (d, J=5.50 Hz, 1H), 7.42 (dd, J=1.65, 8.53 Hz, 1H), 4.74 (dd, J=9.08, 10.73 Hz, 1H), 4.61 (dd, J=2.89, 10.87 Hz, 1H), 3.95 (d, J=2.48 Hz, 1H), 3.86 (d, J=9.08 Hz, 1H), 3.71-3.77 (m, 1H), 3.61-3.66 (m, 1H), 3.40 (s, 3H), 3.33-3.37 (m, 1H).

Example 7 and 8 (Method G Representatives)

(2R,3R,4S,5R,6R)—N-(2-(tert-Butyl)-5-chlorophenyl)-5-hydroxy-6-(hydroxymethyl)-3-methoxy-N-methyl-4-(4-(3,4,5-trifluorophenyl)-1H-1,2,3-triazol-1-yl)tetrahydro-2H-pyran-2-carboxamide (Atropisomer 1 and 2)

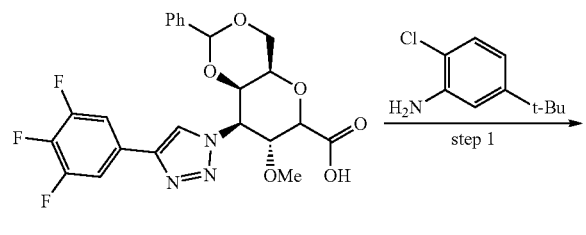

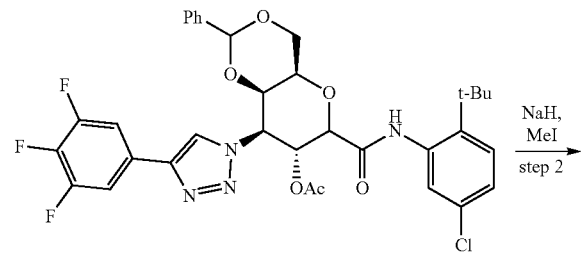

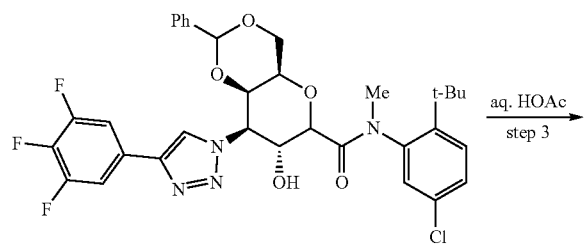

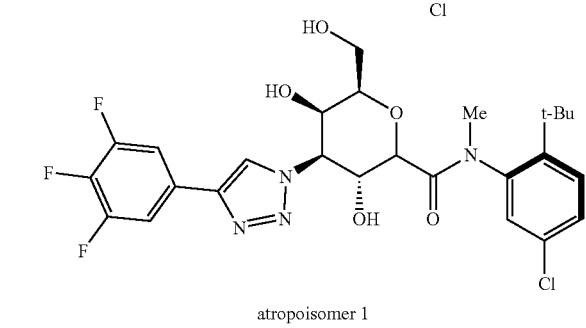

atropoisomer 1
Example 7

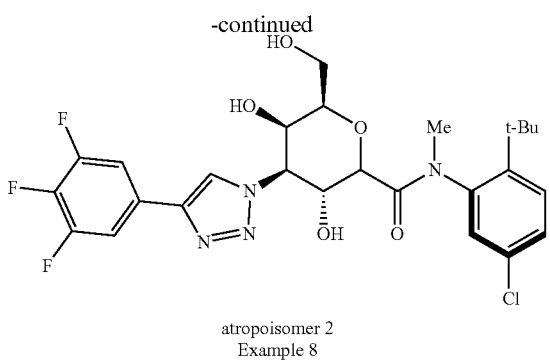

atropoisomer 2
Example 8

Step 1. (4aR,6R,7R,8R,8aR)—N-(2-(tert-Butyl)-5-chlorophenyl)-7-methoxy-2-phenyl-8-(4-(3,4,5-trifluorophenyl)-1H-1,2,3-triazol-1-yl)hexahydropyrano[3,2-d][1,3]dioxine-6-carboxamide A mixture of (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylic acid (30 mg, 0.061 mmol), 2-(tert-butyl)-5-chloroaniline (13.46 mg, 0.073 mmol), pyridine (0.020 mL, 0.244 mmol) and 2,4,6-tripropyl-1,3,5,2,4,6-trioxatriphosphinane 2,4,6-trioxide (50% in EtOAc) (155 mg, 0.244 mmol) in DCE (1.0 mL) in a sealed tube was stirred at 90° C. for 1 h. The mixture was concentrated under vacuum and the residue was subjected to flash chromatography (12 g silica gel, 0-60% ethyl acetate/hexane) to provide the desired product, (4aR,6R,7R,8R,8aR)—N-(2-(tert-butyl)-5-chlorophenyl)-7-methoxy-2-phenyl-8-(4-(3,4,5-trifluorophenyl)-1H-1,2,3-triazol-1-yl)hexahydropyrano[3,2-d][1,3]dioxine-6-carboxamide (39 mg, 0.030 mmol, 48.6% yield) as an off-white solid. LCMS (M+H)$^+$=657.2.

Step 2. (4aR,6R,7R,8R,8aR)—N-(2-(tert-Butyl)-5-chlorophenyl)-7-methoxy-N-methyl-2-phenyl-8-(4-(3,4,5-trifluorophenyl)-1H-1,2,3-triazol-1-yl)hexahydropyrano[3,2-d][1,3]dioxine-6-carboxamide To (4aR,6R,7R,8R,8aR)—N-(2-(tert-butyl)-5-chlorophenyl)-7-methoxy-2-phenyl-8-(4-(3,4,5-trifluorophenyl)-1H-1,2,3-triazol-1-yl)hexahydropyrano[3,2-d][1,3]dioxine-6-carboxamide (39 mg, 0.030 mmol) in DMF (1.0 mL) was added sodium hydride (60% oil dispersion) (5.93 mg, 0.148 mmol), followed by iodomethane (21.06 mg, 0.148 mmol). The resulting mixture was stirred at rt for 1 h, diluted with water (20 mL), and extracted with ethylacetate (40 mL). The organic solution was dried over MgSO$_4$ and concentrated under vacuum. The residue was subjected to flash chromatography (12 g silica gel, 0-90% ethyl acetate/hexane) to afford (4aR,6R,7R,8R,8aR)—N-(2-(tert-butyl)-5-chlorophenyl)-7-methoxy-N-methyl-2-phenyl-8-(4-(3,4,5-trifluorophenyl)-1H-1,2,3-triazol-1-yl)hexahydropyrano[3,2-d][1,3]dioxine-6-carboxamide (30 mg, 0.030 mmol, 99% yield) as an off-white solid. LCMS (M+H)$^+$=671.3.

Step 3. (2R,3R,4S,5R,6R)—N-(2-(tert-Butyl)-5-chlorophenyl)-5-hydroxy-6-(hydroxymethyl)-3-methoxy-N-methyl-4-(4-(3,4,5-trifluorophenyl)-1H-1,2,3-triazol-1-yl)tetrahydro-2H-pyran-2-carboxamide (Atropisomer 1 and 2)

A mixture of (4aR,6R,7R,8R,8aR)—N-(2-(tert-butyl)-5-chlorophenyl)-7-methoxy-N-methyl-2-phenyl-8-(4-(3,4,5- trifluorophenyl)-1H-1,2,3-triazol-1-yl)hexahydropyrano[3,2-d][1,3]dioxine-6-carboxamide (30 mg, 0.030 mmol) in Acetic Acid (0.7 mL) and Water (0.3 mL) at 60° C. overnight. The mixture was diluted with methanol and injected to prep. HPLC (Column: Phenomenex Luna AXIA 30×100 mm C18 5 u; Solvent A: 90% H$_2$O-10% ACN-0.1% TFA, Solvent B: 90% ACN-10% H$_2$O 0.1% TFA; Start % B: 20, Final % B: 60). Two products were isolated. The correct fractions for each product were combined, concentrated under vacuum, basified with saturated NaHCO$_3$ solution, and extracted with dichloromethane (2×25 mL). Removal of the solvent under vacuum provided atropisomer 1 (5 mg, 8.15 μmol, 27.6% yield) and 2 (3 mg, 4.89 μmol, 16.57% yield), as white solids.

Atropisomer 1: LCMS (M+H)$^+$=583.2; $^1$H NMR (400 MHz, methanol-d4) δ 8.63-8.82 (m, 1H), 7.61-7.74 (m, 3H), 7.29-7.46 (m, 1H), 7.03-7.20 (m, 1H), 4.68-4.75 (m, 1H), 4.33-4.45 (m, 1H), 3.98 (d, J=2.64 Hz, 1H), 3.85 (d, J=9.24 Hz, 1H), 3.63-3.66 (m, 1H), 3.43-3.49 (m, 2H), 3.27 (s, 3H), 3.12-3.17 (m, 3H), 1.35-1.45 (m, 9H). hGal-3 (HTRF) IC$_{50}$=0.166 μM.

And atropisomer 2: LCMS (M+H)$^+$=583.2; $^1$H NMR (400 MHz, methanol-d4) δ 8.72 (s, 1H), 7.66 (d, J=8.80 Hz, 3H), 7.43 (dd, J=2.42, 8.80 Hz, 1H), 7.35 (d, J=2.42 Hz, 1H), 4.70 (dd, J=2.86, 10.78 Hz, 1H), 4.52-4.59 (m, 1H), 3.98 (d, J=2.42 Hz, 1H), 3.60-3.75 (m, 3H), 3.23 (s, 3H), 3.12-3.17 (m, 1H), 3.09 (s, 3H), 1.38-1.43 (m, 9H). hGal-3 (HTRF) IC$_{50}$=0.102 μM.

| EX # | Structure/Synthetic Method (D, unless otherwise indicated) | LCMS/ $^1$H NMR (400 MHz, methanol-d$_4$, unless otherwise indicated) | hGal-3 HTRF IC$_{50}$ (μM) |
|---|---|---|---|
| 9 | 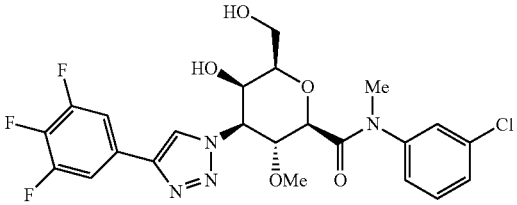<br>A | (M +H)$^+$ = 527.0; $^1$H NMR (500 MHz, methanol-d$_4$) δ 8.71 (s, 1H), 7.69 (dd, J = 8.5, 6.9 Hz, 2H), 7.55-7.46 (m, 3H), 7.42 (br d, J = 7.2 Hz, 1H), 4.75 (dd, J = 10.7, 2.8 Hz, 1H), 4.53-4.46 (m, 1H), 3.99 (d, J = 2.5 Hz, 1H), 3.82 (d, J = 9.1 Hz, 1H), 3.79-3.73 (m, 1H), 3.70-3.64 (m, 1H), 3.41 (br t, J = 5.9 Hz, 1H), 3.37 (s, 3H), 3.14 (s, 3H). | 0.128 |
| 10 | 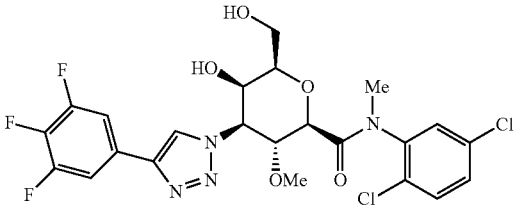<br>C | (M + H)$^+$ = 561.0; $^1$H NMR (500 MHz, methanol-d$_4$) δ 8.73-8.69 (m, 1H), 7.74 (d, J = 2.5 Hz, 1H), 7.69 (dd, J = 8.8, 6.6 Hz, 2H), 7.63 (d, J = 8.8 Hz, 1H), 7.55-7.51 (m, 1H), 4.74 dd, J = 10.7, 3.0 Hz, 1H), 4.54 (dd, J = 10.7, 9.1 Hz, 1H), 4.02-3.96 (m, 1H), 3.74 (dd, J = 11.6, 6.6 Hz, 1H), 3.65 (dd, J = 11.6, 5.8 Hz, 1H), 3.56-3.51 (m, 1H), 3.32-3.31 (m, 1H), 3.28 (s, 3H), 3.15 (s, 3H). | 0.071 |
| 11 | 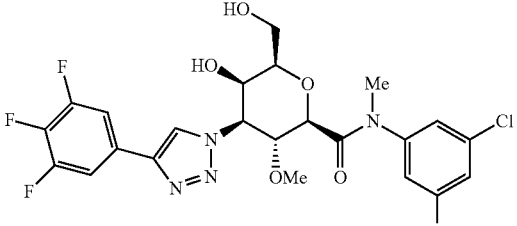<br>C | (M + H)$^+$ = 560.9; $^1$H NMR (500 MHz, DMSO-d$_6$) δ 8.93 (s, 1H), 7.91-7.78 (m, 2H), 7.61 (br s, 1H), 7.53 (br s, 2H), 5.25 (br d, J = 5.5 Hz, 1H), 4.93 (br d, J = 9.9 Hz, 1H), 4.61 (br s, 1H), 4.43 (br t, J = 9.8 Hz, 1H), 3.89 (m, 2H), 3.53 (br dd, J = 13.3, 6.7 Hz, 1H), 3.26 (br s, 3H), 3.04 (s, 3H). | 0.128 |
| 12 | 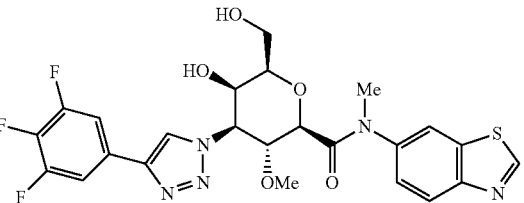 [SMILES: CO[C@@H]1[C@@H](n2cc(-c3cc(F)c(F)c(F)c3)nn2)[C@@H](O)[C@@H](CO)O[C@H]1C(=O)N(C)c1ccc2ncsc2c1] | (M + H)$^+$ = 550.2; δ 9.34 (s, 1H), 8.66-8.68 (m, 1H), 8.24 (d, J = 1.76 Hz, 1H), 8.12-8.21 (m, 1H), 7.57-7.71 (m, 3H), 4.67 (dd, J = 3.08, 10.78 Hz, 1H), 4.49 (dd, J = 9.13, 10.67 Hz, 1H), 3.91 (d, J = 2.42 Hz, 1H), 3.72-3.82 (m, 2H), 3.62 (dd, J = 4.51, 11.77 Hz, 1H), 3.43 (s, 3H), 3.33 (br s, 1H), 3.14 (s, 3H). | 0.022 |
| 13 | 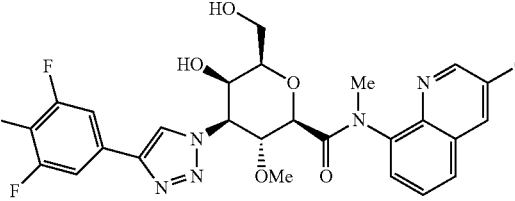 | (M + H)$^+$ = 578.1; δ 8.88 (dd, J = 2.31, 7.81 Hz, 1H), 8.63 (d, J = 12.32 Hz 1H) 8.50 (dd, J = 2.31, 8.25 Hz, 1H), 7.70-8.05 (m, 3H), 7.60-7.69 (m, 2H), 4.29-4.59 (m, 2H), 3.85 (dd, J = 1.43, 19.70 Hz, 1H), 3.58-3.79 (m, 2H), 3.40-3.49 (m, 4H), 3.14-3.24 (m, 4H). | 0.112 |

| EX # | Structure/Synthetic Method (D, unless otherwise indicated) | LCMS/ $^1$H NMR (400 MHz, methanol-$d_4$, unless otherwise indicated) | hGal-3 HTRF IC$_{50}$ (μM) |
|---|---|---|---|
| 14 | | (M + H)$^+$ = 595.1; $^1$H NMR (500 MHz, DMSO-$d_6$) δ 8.99-9.03 (m, 1H), 7.85-7.93 (m, 3H), 7.76-7.81 (m, 2H), 5.32 (br d, J = 5.50 Hz, 1H), 4.83 (br d, J = 10.73 Hz, 1H), 4.66 (br t, J = 5.50 Hz, 1H), 4.43 (br t, J = 9.77 Hz, 1H), 3.76 (br s, 1H), 3.46 (br s, 1H), 3.41 (br s, 1H), 3.17 (s, 3H), 3.03 (s, 3H). | 0.101 |
| 15 | | (M + H)$^+$ = 578.2; δ 8.98-9.07 (m, 1H), 8.70-8.83 (m, 1H), 8.62 (d, J = 11.66 Hz, 1H), 7.83-8.00 (m, 1H), 7.70-7.82 (m, 2H), 7.60-7.67 (m, 2H), 4.30-4.62 (m, 2H), 3.59-3.89 (m, 3H), 3.36-3.49 (m, 4H), 3.12-3.27 (m, 4H). | 1.01 |
| 16 | | (M + H)$^+$ = 548.2; δ 9.36 (s, 1H), 8.66 (s, 1H), 8.25 (d, J = 1.76 Hz, 1H), 8.19 (d, J = 8.58 Hz, 1H), 7.77 (dd, J = 1.87, 10.45 Hz, 1H), 7.69 (td, J = 0.99, 8.36 Hz, 1H), 7.63 (dd, J = 2.20, 8.58 Hz, 1H), 7.55 (t, J = 7.92 Hz, 1H), 4.68 (dd, J = 2.97, 10.67 Hz, 1H), 4.51 (dd, J = 9.02, 10.56 Hz, 1H), 3.92 (d, J = 2.20 Hz, 1H), 3.79-3.83 (m, 1H), 3.73-3.78 (m, 1H), 3.63 (dd, J = 4.51, 11.77 Hz, 1H), 3.44 (s, 3H), 3.34 (br s, 1H), 3.15 (s, 3H). | 0.034 |
| 17 | | (M + H)$^+$ = 552.1; δ 9.18 (s, 1H), 8.76 (s, 1H), 8.63 (d, J = 1.98 Hz, 1H), 8.04 (d, J = 8.80 Hz, 1H), 7.65-7.71 (m, 3H), 5.01 (dd, J = 2.86, 10.56 Hz, 1H), 4.41 (dd, J = 9.35, 10.67 Hz, 1H), 4.16 (d, J = 2.86 Hz, 1H), 4.11-4.15 (m, 1H), 3.83-3.92 (m, 2H), 3.78 (d, J = 3.96 Hz, 1H), 3.19 (s, 3H). | 2.96 |
| 18 | | (M + H)$^+$ = 580.2; δ 9.36 (s, 1H), 8.72 (s, 1H), 8.21 (br s, 1H), 8.16-8.20 (m, 1H), 7.67 (d, J = 7.92 Hz, 2H), 7.59 (br d, J = 8.14 Hz, 1H), 4.67 (dd, J = 3.08, 10.78 Hz, 1H), 4.45-4.54 (m, 1H), 4.01-4.12 (m, 1H), 3.90 (d, J = 2.42 Hz, 1H), 3.69-3.82 (m, 3H), 3.62 (dd, J = 4.51, 11.77 Hz, 1H), 3.26-3.29 (m, 1H), 3.16 (s, 3H), 1.22 (t, J = 7.15 Hz, 3H). | 0.056 |
| 19 | | (M + H)$^+$ = 594.1; δ 9.37 (s, 1H), 8.71 (s, 1H), 8.19 (s, 1H), 8.01-8.18 (m, 1H), 7.63-7.69 (m, 2H), 7.42-7.62 (m, 1H), 4.95-5.05 (m, 1H), 4.61 (dd, J = 2.86, 10.78 Hz, 1H), 4.48 (q, J = 9.98 Hz, 1H), 3.84-3.91 (m, 1H), 3.72 (dd, J = 6.93, 11.55 Hz, 1H), 3.48-3.65 (m, 2H), 3.17 (s, 3H), 3.09-3.15 (m, 1H), 1.22 (br d, J = 6.82 Hz, 3H), 1.15 (br t, J = 7.37 Hz, 3H). | 0.102 |

-continued

| EX # | Structure/Synthetic Method (D, unless otherwise indicated) | LCMS/ $^1$H NMR (400 MHz, methanol-d$_4$, unless otherwise indicated) | hGal-3 HTRF IC$_{50}$ (μM) |
|---|---|---|---|
| 20 | | (M + H)$^+$ = 566.2; δ 9.35 (s, 1H), 8.55 (d, J = 3.30 Hz, 1H), 8.25 (s, 1H), 8.18 (d, J = 8.58 Hz, 1H), 7.85-7.96 (m, 1H), 7.51-7.67 (m, 1H), 7.37-7.51 (m, 1H), 4.72 (dd, J = 2.86, 10.78 Hz, 1H), 4.48-4.55 (m, 1H), 3.93 (br d, J = 2.20 Hz, 1H), 3.81 (br d, J = 9.02 Hz, 1H), 3.76 (br dd, J = 7.37, 11.77 Hz, 1H), 3.62 (br dd, J = 4.51, 11.77 Hz, 1H), 3.43 (s, 3H), 3.34 (br s, 1H), 3.13 (s, 3H). | 0.021 |
| 21 | | (M + H)$^+$ = 612.1; δ 9.34 (s, 1H), 8.73 (s, 1H), 8.21-8.28 (m, 1H), 8.05-8.21 (m, 1H), 7.62 (br d, J = 7.70 Hz, 3H), 4.69 (dd, J = 2.86, 10.78 Hz, 1H), 4.47-4.55 (m, 1H), 3.91 (br d, J = 2.20 Hz, 1H), 3.78-3.84 (m, 1H), 3.70-3.78 (m, 1H), 3.59-3.67 (m, 1H), 3.43 (s, 3H), 3.33-3.36 (m, 1H), 3.12-3.17 (m, 3H). | 0.040 |
| 22 | | (M + H)$^+$ = 592.1; δ 9.35 (s, 1H), 8.67 (s, 1H), 8.25 (d, J = 1.76 Hz, 1H), 8.18 (d, J = 8.58 Hz, 1H), 7.72-7.77 (m, 1H), 7.66-7.72 (m, 1H), 7.62 (td, J = 2.28, 8.42 Hz, 2H), 4.68 (dd, J = 2.97, 10.67 Hz, 1H), 4.51 (dd, J = 9.02, 10.78 Hz, 1H), 3.92 (d, J = 2.42 Hz, 1H), 3.79-3.83 (m, 1H), 3.74-3.78 (m, 1H), 3.63 (dd, J = 4.62, 11.66 Hz, 1H), 3.44 (s, 3H), 3.34 (br s, 1H), 3.15 (s, 3H). | 0.033 |
| 23 | | (M + H)$^+$ = 619.3; δ 8.73 (s, 1H), 8.00-8.18 (m, 1H), 7.75-7.85 (m, 1H), 7.68 (br d, J = 5.72 Hz, 3H), 2.64-5.12 (m, 15H), 1.10-1.40 (m, 3H). | 0.026 |
| 24 | | (M + H)$^+$ = 557.2; δ 8.65-8.69 (m, 1H), 7.66 (dd, J = 6.71, 8.69 Hz, 2H), 7.27-7.53 (m, 2H), 7.15 (d, J = 8.80 Hz, 1H), 4.67-4.75 (m, 1H), 4.47 (dd, J = 9.02, 10.78 Hz, 1H), 3.95-3.99 (m, 1H), 3.86-3.91 (m, 3H), 3.68-3.77 (m, 1H), 3.60-3.68 (m, 2H), 3.33-3.43 (m, 1H), 3.20-3.26 (m, 3H), 3.11-3.16 (m, 3H). | 0.092 |
| 25 | | (M + H)$^+$ = 561.2; δ 8.65-8.69 (m, 1H), 7.39-7.71 (m, 5H), 4.71 (dd, J = 3.08, 10.78 Hz, 1H), 4.49 (dd, J = 8.91, 10.67 Hz, 1H), 3.91-3.99 (m, 1H), 3.67-3.83 (m, 1H), 3.57-3.65 (m, 1H), 3.50 (d, J = 8.80 Hz, 1H), 3.31-3.40 (m, 1H), 3.23-3.28 (m, 3H), 3.10-3.15 (m, 3H). | 2.53 |

| EX # | Structure/Synthetic Method (D, unless otherwise indicated) | LCMS/ ¹H NMR (400 MHz, methanol-d₄, unless otherwise indicated) | hGal-3 HTRF IC$_{50}$ (μM) |
|---|---|---|---|
| 26 | [Structure: triazole linked to sugar with OMe, OH, HO groups; N-Me amide to aryl with CF₃, F, Cl substituents; 3,4,5-trifluorophenyl] | (M + H)⁺ = 613.2; δ 8.67-8.80 (m, 1H), 7.74-7.90 (m, 1H), 7.62-7.74 (m, 3H), 4.73 (dd, J = 2.97, 10.67 Hz, 1H), 4.51 (s, 1H), 4.34 (m, 5H), 3.24-3.29 (m, 3H), 3.03-3.15 (m, 3H). | 3.74 |
| 27 | [Structure: triazole linked to sugar with OMe, OH, HO groups; N-Me amide to aryl with N(Me)₂, Cl substituents; 3,4,5-trifluorophenyl] | (M + H)⁺ = 570.3; δ 8.63-8.73 (m, 1H), 7.62-7.70 (m, 2H), 7.46 (d, J = 2.64 Hz, 1H), 7.28-7.36 (m, 1H), 7.10 (d, J = 8.80 Hz, 1H), 4.75 (dd, J = 2.86, 10.78 Hz, 1H), 4.56 (dd, J = 9.02, 10.78 Hz, 1H), 3.96-4.03 (m, 1H), 3.79-3.87 (m, 1H), 3.62-3.79 (m, 2H), 3.40-3.52 (m, 1H), 3.23 (s, 3H), 3.02-3.15 (m, 3H), 2.74-2.79 (m, 6H). | 0.151 |
| 28 | [Structure: triazole linked to sugar with OMe, OH, HO groups; N-Me amide to aryl with OPh, Cl substituents; 3,4,5-trifluorophenyl] | (M + H)⁺ = 619.3; δ 8.68-8.76 (m, 1H), 7.62-7.75 (m, 3H), 7.32-7.50 (m, 3H), 7.16-7.27 (m, 1H), 7.06-7.15 (m, 2H), 6.91-7.04 (m, 1H), 4.82 (br d, J = 2.64 Hz, 1H), 4.31-4.60 (m, 1H), 4.00-4.15 (m, 1H), 3.84 (d, J = 8.80 Hz, 1H), 3.69-3.80 (m, 1H), 3.56-3.68 (m, 1H), 3.41-3.53 (m, 1H), 3.26-3.31 (m, 3H), 3.00-3.20 (m, 3H). | 0.425 |
| 29 | [Structure: triazole linked to sugar with OMe, OH, HO groups; N-Me amide to aryl with t-Bu, Cl substituents; 3-chloro-4,5-difluorophenyl] Atropoisomer 1 | (M + H)⁺ = 599.2; ¹H NMR (500 MHz, DMSO-d₆) δ 8.96-9.00 (m, 1H), 7.82 (br d, J = 8.54 Hz, 2H), 7.62 (d, J = 8.85 Hz, 1H), 7.41 (dd, J = 2.29, 8.70 Hz, 1H), 6.92 (d, J = 2.14 Hz, 1H), 5.32 (d, J = 6.10 Hz, 1H), 4.74-4.79 (m, 1H), 4.60 (t, J = 5.19 Hz, 1H), 4.23-4.29 (m, 1H), 3.74-3.79 (m, 1H), 3.38 (br s, 2H), 3.06 (s, 3H), 2.45-2.46 (m, 3H), 1.31 (s, 9H). | 0.879 |
| 30 | [Structure: triazole linked to sugar with OMe, OH, HO groups; N-Me amide to aryl with t-Bu, Cl substituents; 3-chloro-4,5-difluorophenyl] Atropoisomer 2 | (M + H)⁺ = 599.3; ¹H NMR (500 MHz, DMSO-d₆) δ 8.93-8.97 (m, 1H), 7.80 (br d, J = 8.24 Hz, 2H), 7.60 (d, J = 9.16 Hz, 1H), 7.40 (br d, J = 8.85 Hz, 1H), 7.20 (d, J = 1.22 Hz, 1H), 5.32 (d, J = 6.10 Hz, 1H), 4.69-4.72 (m, 1H), 4.35-4.43 (m, 1H), 3.60-3.66 (m, 3H), 3.40 (br s, 1H), 2.96 (s, 3H), 2.46 (br s, 3H), 1.27 (s, 9H). | 0.130 |

| EX # | Structure/Synthetic Method (D, unless otherwise indicated) | LCMS/ $^1$H NMR (400 MHz, methanol-d$_4$, unless otherwise indicated) | hGal-3 HTRF IC$_{50}$ (μM) |
|---|---|---|---|
| 31 | Atropoisomer 1 | (M + H)$^+$ = 581.3; $^1$H NMR (500 MHz, methanol-d$_4$) δ 8.68 (s, 1H), 7.75-7.81 (m, 1H), 7.68 (dd, J = 9.51, 11.11 Hz, 2H), 7.55 (s, 1H), 7.41 (dd, J = 2.19, 8.84 Hz, 1H), 7.07 (d, J = 2.27 Hz, 1H), 4.72 (dd, J = 2.82, 10.90 Hz, 1H), 4.39 (t, J = 9.97 Hz, 1H), 3.98 (d, J = 2.19 Hz, 1H), 3.86 (d, J = 9.09 Hz, 1H), 3.65 (d, J = 5.89 Hz, 2H), 3.46 (t, J = 6.31 Hz, 1H), 3.27 (s, 3H), 3.16 (s, 3H), 1.43 (s, 9H). | 0.529 |
| 32 | Atropoisomer 2 | (M + H)$^+$ = 581.1; $^1$H NMR (500 MHz, methanol-d$_4$) δ 8.71 (s, 1H), 7.76-7.79 (m, 1H), 7.69 (dd, J = 1.22, 8.37 Hz, 1H), 7.66 (d, J = 8.84 Hz, 1H), 7.54 (d, J = 8.25 Hz, 2H), 7.35 (d, J = 2.36 Hz, 1H), 4.70 (dd, J = 2.95, 10.77 Hz, 1H), 4.56 (dd, J = 9.13, 10.64 Hz, 1H), 3.98 (d, J = 2.44 Hz, 1H), 3.69-3.71 (m, 1H), 3.64 (s, 1H), 3.23 (s, 3H), 3.19 (s, 1H), 3.15 (s, 1H), 3.09 (s, 3H), 1.41 (s, 9H). | 0.108 |
| 33 |  | (M + H)$^+$ = 604.1; $^1$H NMR (500 MHz, DMSO-d$_6$) δ 8.91-9.01 (m, 1H), 8.75 (d, J = 1.83 Hz, 1H), 8.09 (d, J = 1.83 Hz, 1H), 7.79-7.86 (m, 2H), 7.55-7.62 (m, 2H), 7.34-7.46 (m, 3H), 5.39 (d, J = 5.80 Hz, 1H), 4.92 (br dd, J = 2.90, 10.83 Hz, 1H), 4.81 (t, J = 5.34 Hz, 1H), 4.46 (t, J = 9.77 Hz, 1H), 3.91 (d, J = 8.85 Hz, 1H), 3.73-3.82 (m, 1H), 3.03-3.15 (m, 3H), 2.83-2.92 (m, 1H), 2.68 (s, 3H). | 0.087 |
| 34 |  | (M + H)$^+$ = 605.1; $^1$H NMR (500 MHz, methanol-d$_4$) δ 8.65-8.73 (m, 1H), 7.77 (d, J = 8.80 Hz, 1H), 7.62-7.72 (m, 3H), 7.43 (br dd, J = 2.48, 8.53 Hz, 1H), 4.68-4.74 (m, 1H), 4.48-4.58 (m, 1H), 3.94-4.03 (m, 1H), 3.71 (dd, J = 6.74, 11.42 Hz, 1H), 3.64 (t, J = 6.19 Hz, 1H), 3.49 (d, J = 8.80 Hz, 1H), 3.33-3.42 (m, 1H), 3.25 (s, 3H), 3.13-3.17 (m, 3H). | 0.122 |
| 35 |  | (M + H)$^+$ = 564.1; $^1$H NMR (500 MHz, methanol-d$_4$) δ 9.35 (s, 1H), 8.67 (s, 1H), 8.25 (s, 1H), 8.18 (d, J = 8.80 Hz, 1H), 8.05 (d, J = 1.65 Hz, 1H), 7.79 (dd, J = 1.79, 8.39 Hz, 1H), 7.61-7.64 (m, 1H), 7.58-7.61 (m, 1H), 4.68 (dd, J = 2.75, 10.73 Hz, 1H), 4.51 (t, J = 9.90 Hz, 1H), 3.91 (br d, J = 2.48 Hz, 1H), 3.80 (br d, J = 9.08 Hz, 1H), 3.76 (br dd, J = 7.29, 11.69 Hz, 1H), 3.63 (dd, J = 4.54, 11.69 Hz, 1H), 3.43 (s, 3H), 3.33-3.34 (m, 1H), 3.14 (s, 3H). | 0.071 |

| EX # | Structure/Synthetic Method (D, unless otherwise indicated) | LCMS/ ¹H NMR (400 MHz, methanol-d₄, unless otherwise indicated) | hGal-3 HTRF IC$_{50}$ (μM) |
|---|---|---|---|
| 36 | | (M + H)⁺ = 578.1; ¹H NMR (500 MHz, DMSO-d₆) δ 9.00 (d, J = 4.58 Hz, 1H), 8.88-8.95 (m, 1H), 8.18-8.25 (m, 1H), 7.79-7.87 (m, 3H), 7.67-7.79 (m, 2H), 5.37 (d, J = 6.10 Hz, 1H), 4.65-4.74 (m, 1H), 4.40 (t, J = 9.77 Hz, 1H), 3.65-3.74 (m, 1H), 3.42 (br d, J = 8.85 Hz, 1H), 3.22 (br t, J = 6.26 Hz, 1H), 3.02-3.11 (m, 3H), 2.81-2.92 (m, 1H), 2.54 (s, 3H). | 0.558 |
| 37 | | (M + H)⁺ = 566.2; ¹H NMR (500 MHz, methanol-d₄) δ 9.34 (s, 1H), 8.52 (d, J = 3.58 Hz, 1H), 8.21-8.27 (m, 1H), 8.17 (d, J = 8.53 Hz, 1H), 7.98 (dd, J = 6.33, 9.63 Hz, 1H), 7.62 (dd, J = 1.93, 8.80 Hz, 1H), 7.48 (dd, J = 6.05, 9.90 Hz, 1H), 4.71 (dd, J = 3.03, 10.73 Hz, 1H), 4.50 (dd, J = 9.22, 10.59 Hz, 1H), 3.92 (d, J = 2.48 Hz, 1H), 3.80 (d, J = 9.08 Hz, 1H), 3.75 (dd, J = 7.15, 11.83 Hz, 1H), 3.63 (br d, J = 4.40 Hz, 1H), 3.42 (s, 3H), 3.32-3.35 (m, 1H), 3.12 (s, 3H). | 0.050 |
| 38 | | (M + H)⁺ = 611.2; ¹H NMR (500 MHz, methanol-d₄) δ 8.71-8.76 (m, 1H), 7.84-7.90 (m, 1H), 7.79 (d, J = 1.93 Hz, 1H), 7.69-7.73 (m, 1H), 7.67 (d, J = 7.70 Hz, 2H), 4.71 (br dd, J = 2.89, 10.87 Hz, 1H), 4.55 (dd, J = 8.94, 10.87 Hz, 1H), 3.93-3.96 (m, 1H), 3.69-3.78 (m, 1H), 3.60-3.65 (m, 1H), 3.50 (d, J = 3.03 Hz, 1H), 3.25-3.29 (m, 3H), 3.19-3.24 (m, 1H), 3.10-3.17 (m, 3H). | 0.064 |
| 39 | | (M + H)⁺ = 582.1; δ 9.35 (s, 1H), 8.75 (s, 1H), 8.25 (d, J = 1.54 Hz, 1H), 8.18 (d, J = 8.80 Hz, 1H), 7.85 (dd, J = 1.87, 8.69 Hz, 1H), 7.62 (dd, J = 2.09, 8.69 Hz, 1H), 7.52-7.59 (m, 1H), 4.73 (dd, J = 2.97, 10.67 Hz, 1H), 4.51 (dd, J = 9.13, 10.67 Hz, 1H), 3.95 (d, J = 2.42 Hz, 1H), 3.81 (d, J = 9.02 Hz, 1H), 3.76 (dd, J = 7.15, 11.77 Hz, 1H), 3.63 (dd, J = 4.51, 11.77 Hz, 1H), 3.43 (s, 3H), 3.34 (br d, J = 5.28 Hz, 1H), 3.15 (s, 3H). | 0.018 |
| 40 | | (M + H)⁺ = 541.2; δ 8.74-8.78 (m, 1H), 7.70 (dd, J = 6.60, 8.80 Hz, 2H), 7.21-7.42 (m, 4H), 4.89-5.04 (m, 1H), 4.76-4.83 (m, 1H), 4.66 (d, J = 3.30 Hz, 1H), 4.41-4.56 (m, 2H), 4.06-4.12 (m, 1H), 3.67-3.90 (m, 3H), 3.12-3.23 (m, 3H), 2.93-3.10 (m, 3H). | 1.85 |
| 41 | | (M + H)⁺ = 580.2; δ 9.26 (s, 1H), 8.62 (s, 1H), 8.32 (s, 1H), 8.16-8.19 (m, 1H), 8.12-8.16 (m, 1H), 7.97 (dd, J = 1.54, 8.58 Hz, 1H), 7.82-7.89 (m, 3H), 7.65 (s, 1H), 7.57 (dd, J = 1.98, 8.58 Hz, 1H), 7.44 (dd, J = 2.09, 8.69 Hz, 1H), 4.62 (dd, J = 2.86, 10.78 Hz, 1H), 4.45 (dd, J = 9.13, 10.67 Hz, 1H), 3.98 (d, J = 2.42 Hz, 1H), 3.78-3.82 (m, 1H), 3.73-3.78 (m, 1H), 3.63-3.70 (m, 1H), 3.43 (s, 3H), 3.27-3.30 (m, 1H), 3.12 (s, 3H). | 3.27 |

| EX # | Structure/Synthetic Method (D, unless otherwise indicated) | LCMS/ $^1$H NMR (400 MHz, methanol-$d_4$, unless otherwise indicated) | hGal-3 HTRF IC$_{50}$ (μM) |
|---|---|---|---|
| 42 | | (M + H)$^+$ = 610.2; δ 9.35 (s, 1H), 8.55 (d, J = 3.30 Hz, 1H), 8.24 (d, J = 1.98 Hz, 1H), 8.18 (d, J = 8.58 Hz, 1H), 7.82-7.89 (m, 1H), 7.62 (dd, J = 2.09, 8.69 Hz, 1H), 7.50-7.58 (m, 1H), 4.71 (dd, J = 2.86, 10.78 Hz, 1H), 4.52 (dd, J = 9.02, 10.56 Hz, 1H), 3.93 (d, J = 2.42 Hz, 1H), 3.80 (d, J = 9.02 Hz, 1H), 3.76 (dd, J = 7.26, 11.66 Hz, 1H), 3.60-3.65 (m, 1H), 3.43 (s, 3H), 3.32-3.35 (m, 1H), 3.13 (s, 3H). | 0.015 |
| 43 | | (M + H)$^+$ = 582.3; $^1$H NMR (500 MHz, methanol-$d_4$) δ 9.35 (s, 1H), 8.55 (d, J = 3.58 Hz, 1H), 8.22-8.28 (m, 1H), 8.18 (d, J = 8.53 Hz, 1H), 8.02-8.11 (m, 1H), 7.62 (dd, J = 1.93, 8.53 Hz, 1H), 7.50 (dd, J = 1.38, 8.53 Hz, 1H), 4.72 (dd, J = 3.03, 10.73 Hz, 1H), 4.52 (dd, J = 9.22, 10.59 Hz, 1H), 3.94 (d, J = 2.75 Hz, 1H), 3.81 (d, J = 9.08 Hz, 1H), 3.76 (dd, J = 7.15, 11.83 Hz, 1H), 3.63 (dd, J = 4.68, 11.83 Hz, 1H), 3.43 (s, 3H), 3.32-3.36 (m, 1H), 3.13 (s, 3H). | 0.014 |
| 44 | | (M + H)$^+$ = 549.1; δ 8.56 (s, 1H), 7.95 (s, 1H), 7.90-7.94 (m, 1H), 7.64 (d, J = 5.28 Hz, 1H), 7.57 (dd, J = 6.60, 8.58 Hz, 2H), 7.42 (d, J = 5.50 Hz, 1H), 7.35 (dd, J = 1.98, 8.36 Hz, 1H), 4.59 (dd, J = 2.86, 10.78 Hz, 1H), 4.40 (dd, J = 9.13, 10.67 Hz, 1H), 3.95 (d, J = 2.20 Hz, 1H), 3.83 (d, J = 9.02 Hz, 1H), 3.71-3.78 (m, 1H), 3.68 (d, J = 5.28 Hz, 1H), 3.41 (s, 3H), 3.29 (s, 1H), 3.11 (s, 3H). | 0.095 |

Section B

General Synthetic Scheme B1. Preparation of C2-hydroxy derivatives listed on Table B1

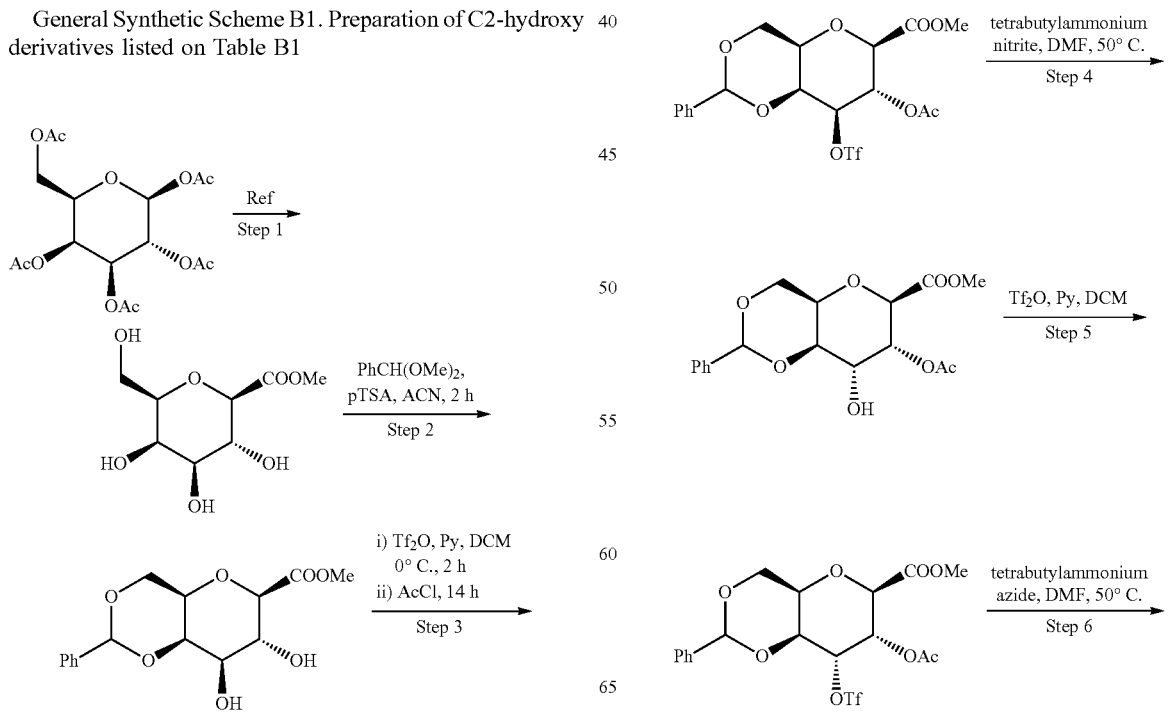

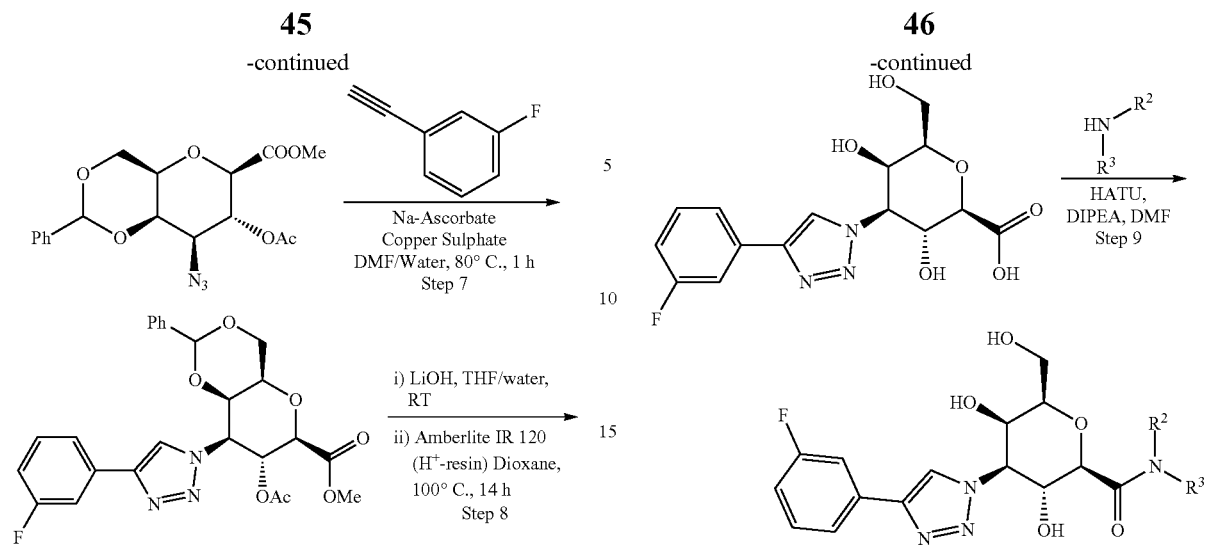
TABLE B1
| EX # | Structure | Amine Fragment | hGal-3 ELISA IC$_{50}$ (μM) |
|---|---|---|---|
| B1 | 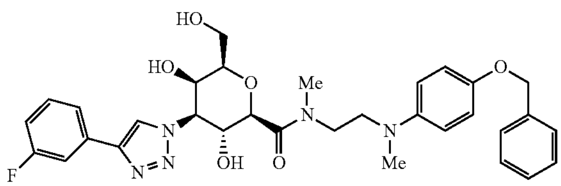 [SMILES: CN(CCN(C)c1ccc(OCc2ccccc2)cc1)C(=O)[C@@H]1O[C@H](CO)[C@H](O)[C@H](n2cc(-c3cccc(F)c3)nn2)[C@H]1O] | | 0.41 |
| B2 | 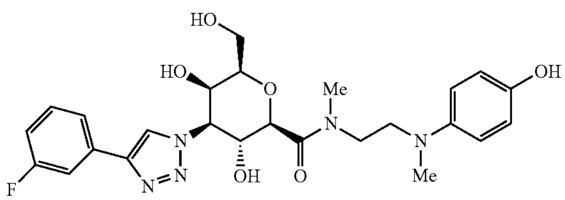 [SMILES: CN(CCN(C)c1ccc(O)cc1)C(=O)[C@@H]1O[C@H](CO)[C@H](O)[C@H](n2cc(-c3cccc(F)c3)nn2)[C@H]1O] | | 0.46 |
| B3 | 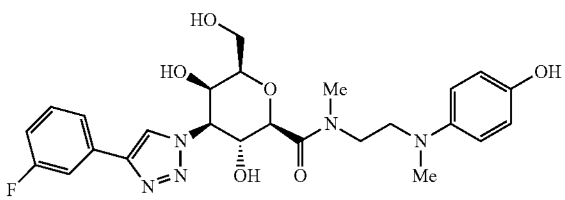 [SMILES: CN(CCN(C)c1ccc(O)cc1)C(=O)[C@@H]1O[C@H](CO)[C@H](O)[C@H](n2cc(-c3cccc(F)c3)nn2)[C@H]1O] | | 0.29 |
| B4 | 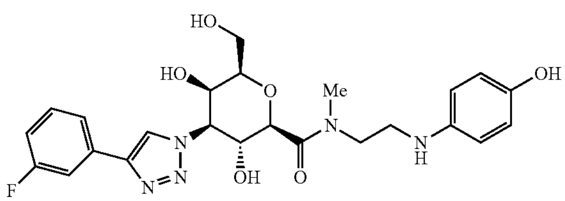 [SMILES: CN(CCNc1ccc(O)cc1)C(=O)[C@@H]1O[C@H](CO)[C@H](O)[C@H](n2cc(-c3cccc(F)c3)nn2)[C@H]1O] | | 0.16 |
| B5 | 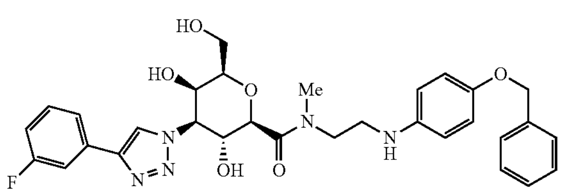 [SMILES: CN(CCNc1ccc(OCc2ccccc2)cc1)C(=O)[C@@H]1O[C@H](CO)[C@H](O)[C@H](n2cc(-c3cccc(F)c3)nn2)[C@H]1O] | | 0.68 |

TABLE B1-continued
| EX # | Structure | Amine Fragment | hGal-3 ELISA IC$_{50}$ (μM) |
|---|---|---|---|
| B6 | 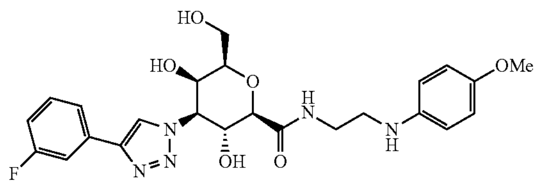 [SMILES: COc1ccc(NCCNC(=O)[C@@H]2O[C@H](CO)[C@H](O)[C@H](n3cc(-c4cccc(F)c4)nn3)[C@H]2O)cc1] | | 0.10 |
| B7 | 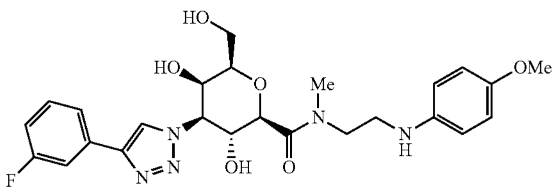 [SMILES: COc1ccc(NCCN(C)C(=O)[C@@H]2O[C@H](CO)[C@H](O)[C@H](n3cc(-c4cccc(F)c4)nn3)[C@H]2O)cc1] | | 0.20 |
| B8 | 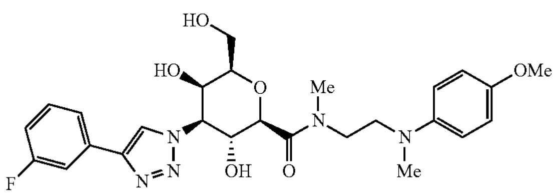 [SMILES: COc1ccc(N(C)CCN(C)C(=O)[C@@H]2O[C@H](CO)[C@H](O)[C@H](n3cc(-c4cccc(F)c4)nn3)[C@H]2O)cc1] | | 0.93 |
| B9 | 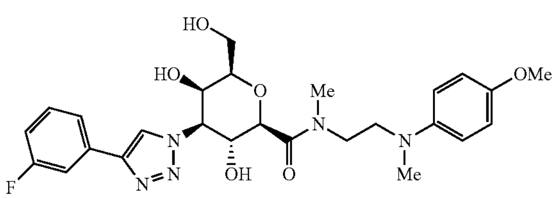 [SMILES: COc1ccc(N(C)CCN(C)C(=O)[C@@H]2O[C@H](CO)[C@H](O)[C@H](n3cc(-c4cccc(F)c4)nn3)[C@H]2O)cc1] | | 0.15 |
General Synthetic Scheme B2. Preparation C2-hydroxy derivatives listed in Table B2
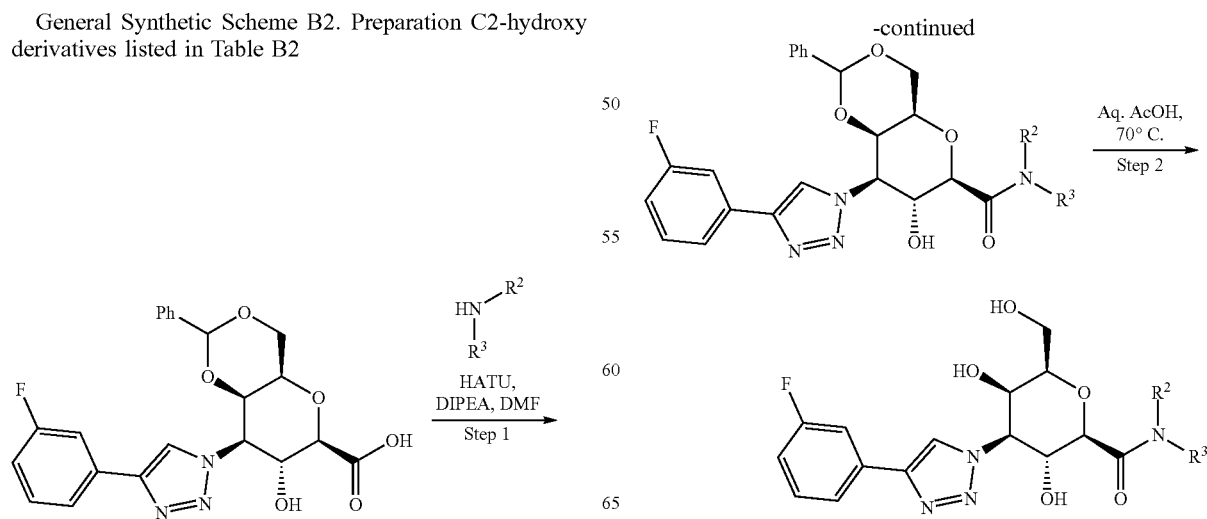

TABLE B2
| EX # | Structure | Amine Fragment | hGal-3 ELISA IC$_{50}$ (µM) |
|---|---|---|---|
| B10 | 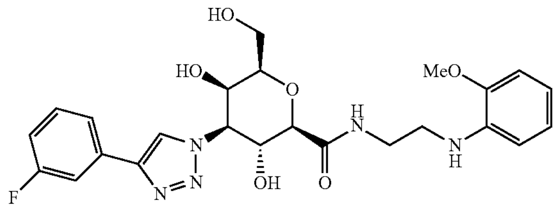 [SMILES: COc1ccccc1NCCNC(=O)[C@@H]1O[C@H](CO)[C@H](O)[C@H](n2cc(-c3cccc(F)c3)nn2)[C@H]1O] | | 0.46 |
| B11 | 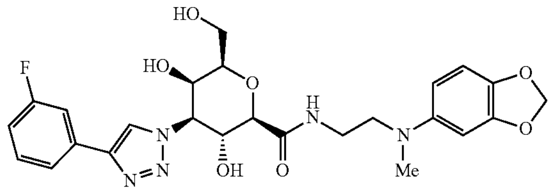 [SMILES: CN(CCNC(=O)[C@@H]1O[C@H](CO)[C@H](O)[C@H](n2cc(-c3cccc(F)c3)nn2)[C@H]1O)c1ccc2c(c1)OCO2] | | 0.36 |
| B12 | 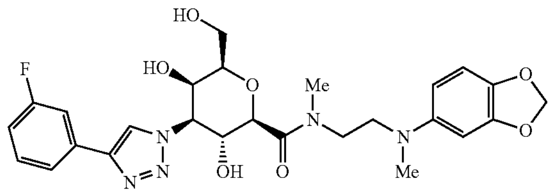 [SMILES: CN(CCN(C)c1ccc2c(c1)OCO2)C(=O)[C@@H]1O[C@H](CO)[C@H](O)[C@H](n2cc(-c3cccc(F)c3)nn2)[C@H]1O] | | 0.38 |
| B13 | 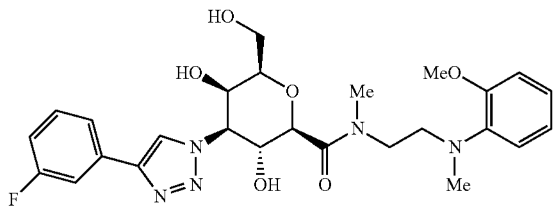 [SMILES: COc1ccccc1N(C)CCN(C)C(=O)[C@@H]1O[C@H](CO)[C@H](O)[C@H](n2cc(-c3cccc(F)c3)nn2)[C@H]1O] | | 0.62 |
General Synthetic Scheme B3. Preparation of derivatives listed in Table B3
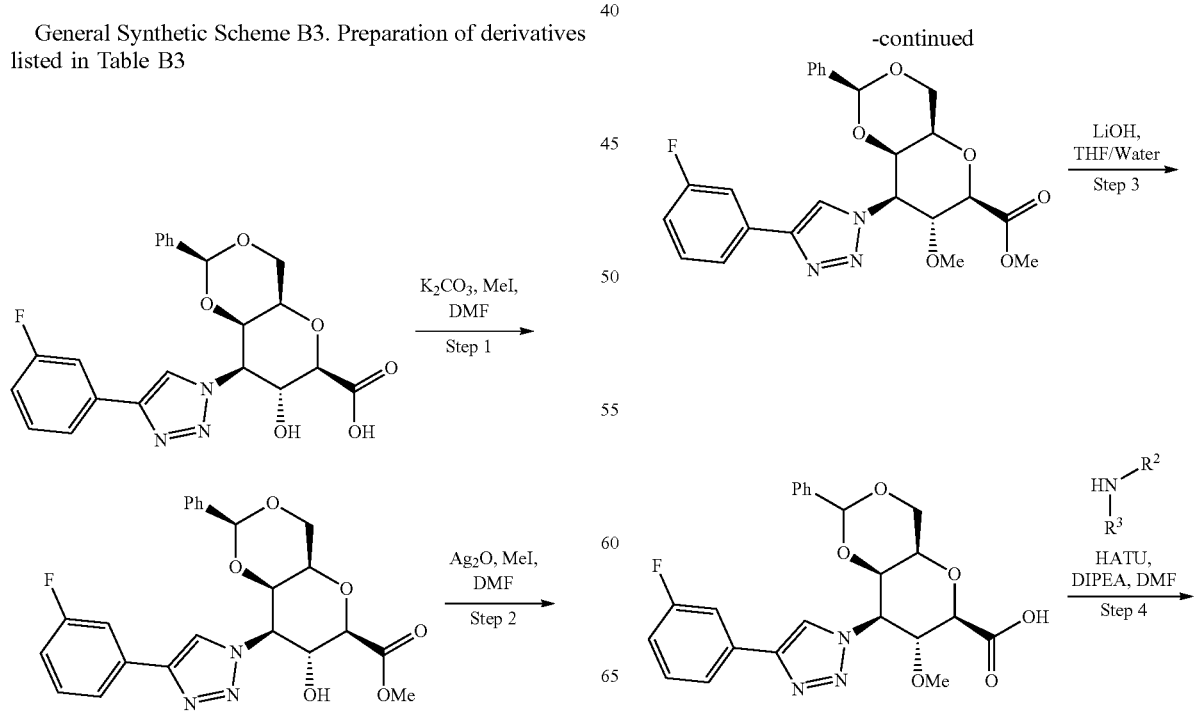

-continued
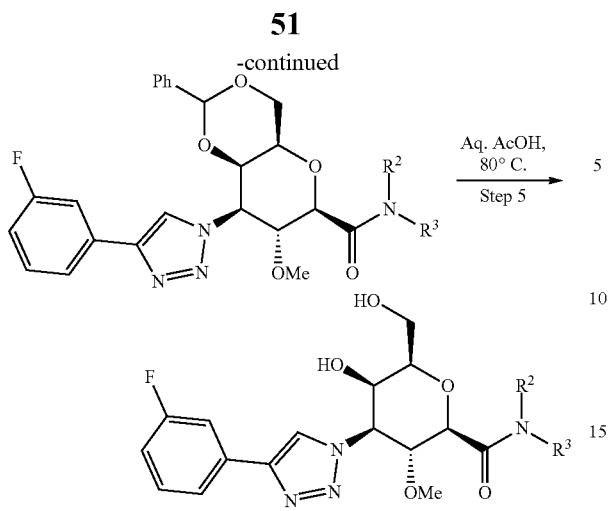
TABLE B3
| EX # | Structure | Amine Fragment | hGal-3 ELISA IC$_{50}$ (μM) |
|---|---|---|---|
| B14 | 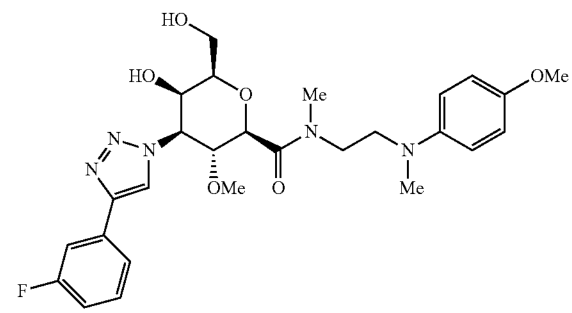 [SMILES: COc1ccc(N(C)CCN(C)C(=O)[C@@H]2O[C@H](CO)[C@H](O)[C@H](n3cc(-c4cccc(F)c4)nn3)[C@H]2OC)cc1] | | 0.33 |
| B15 | 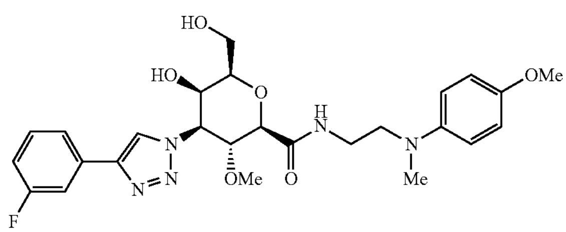 [SMILES: COc1ccc(N(C)CCNC(=O)[C@@H]2O[C@H](CO)[C@H](O)[C@H](n3cc(-c4cccc(F)c4)nn3)[C@H]2OC)cc1] | | 0.15 |
| B16 | 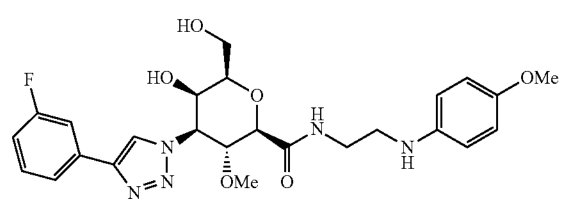 [SMILES: COc1ccc(NCCNC(=O)[C@@H]2O[C@H](CO)[C@H](O)[C@H](n3cc(-c4cccc(F)c4)nn3)[C@H]2OC)cc1] | | 0.48 |
| B17 | 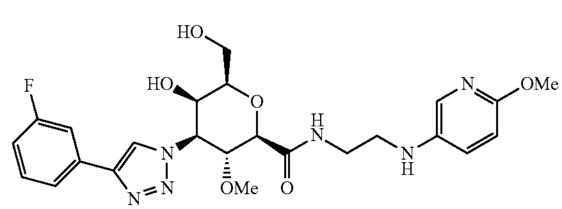 | | 0.74 |

TABLE B3-continued
| EX # | Structure | Amine Fragment | hGal-3 ELISA IC$_{50}$ (μM) |
|---|---|---|---|
| B18 | 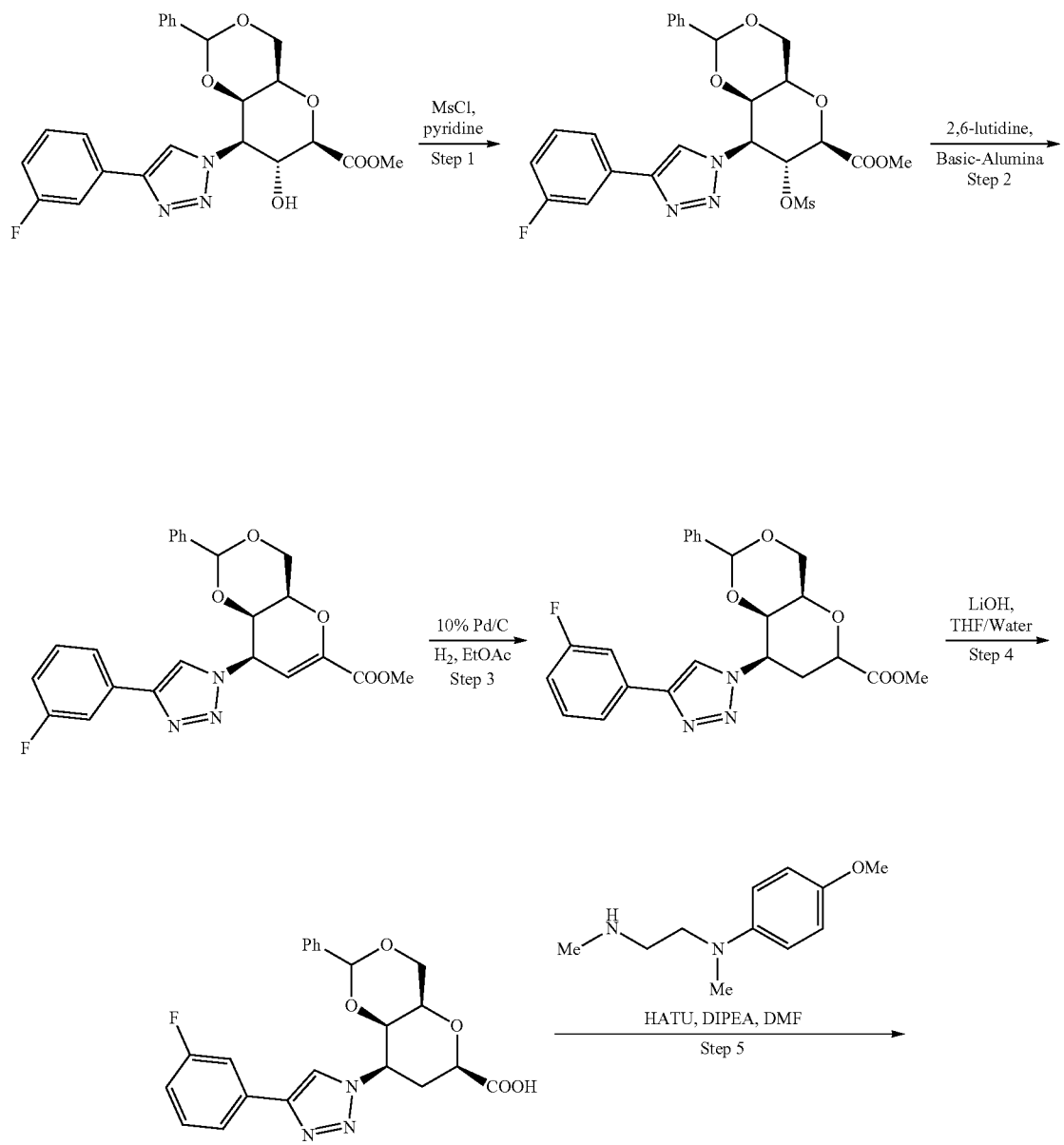 | | 0.68 |
Example B19

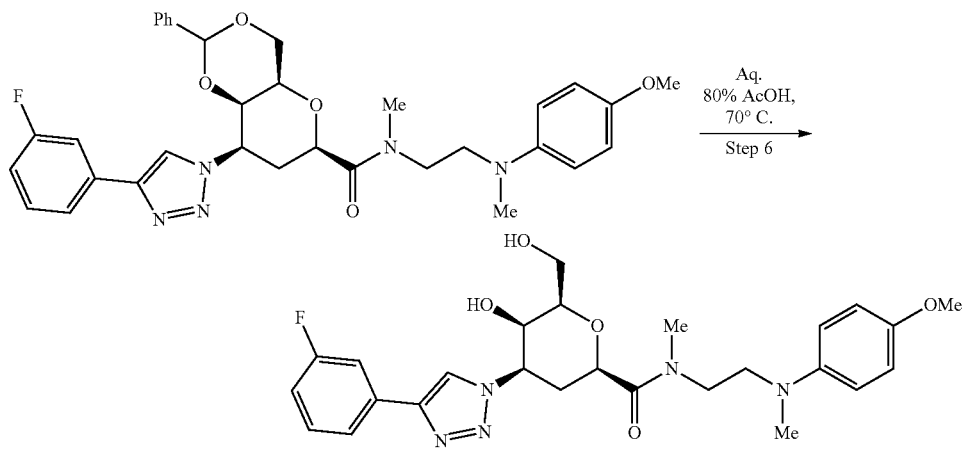
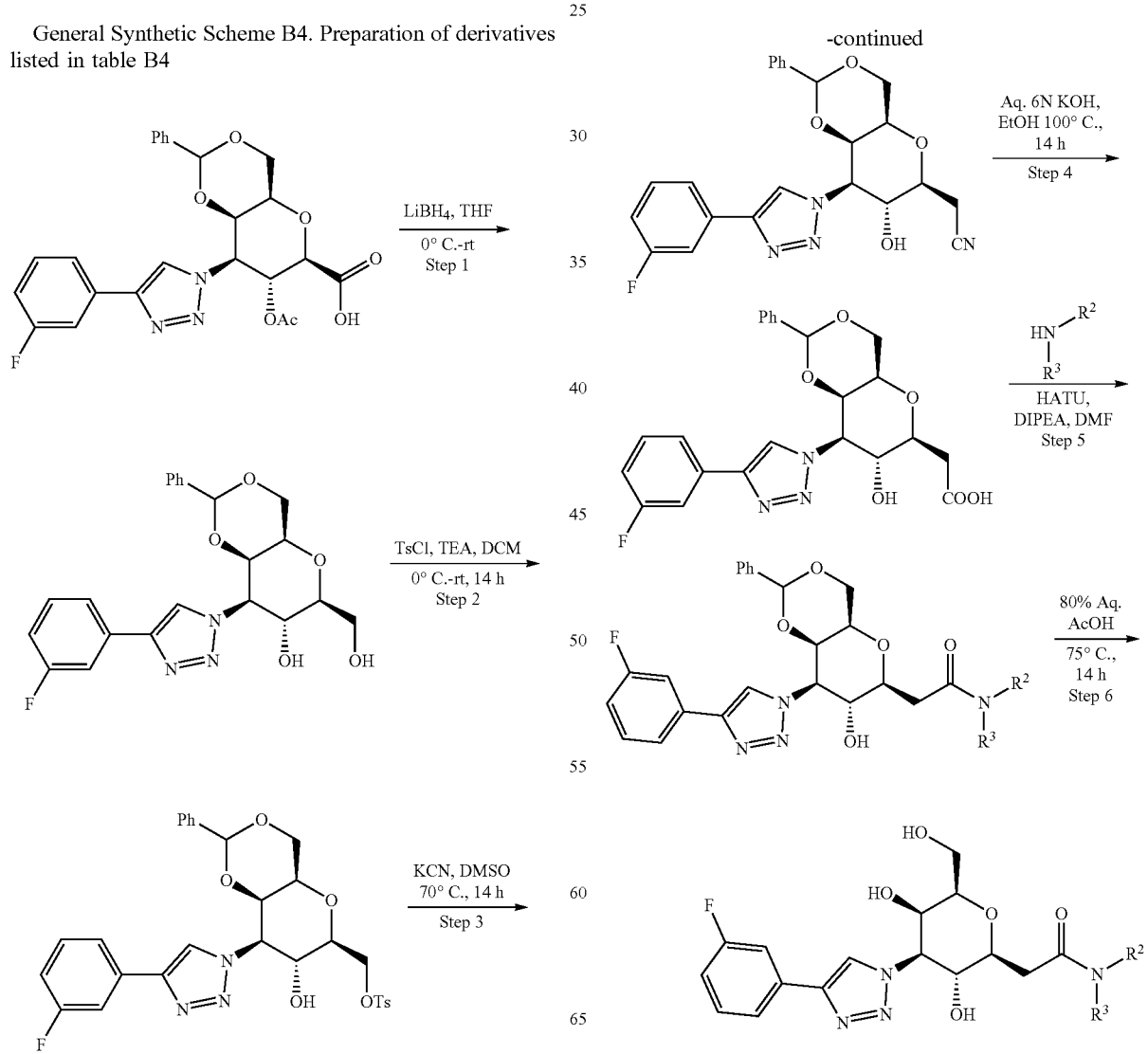
General Synthetic Scheme B4. Preparation of derivatives listed in table B4

TABLE B4
| EX # | Structure | Amine Fragment | hGal-3 ELISA IC$_{50}$ (μM) |
|---|---|---|---|
| B20 | 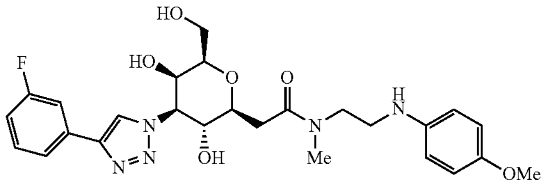 [SMILES: COc1ccc(NCCN(C)C(=O)C[C@@H]2O[C@H](CO)[C@H](O)[C@H](n3cc(-c4cccc(F)c4)nn3)[C@H]2O)cc1] | | 0.29 |
| B21 | 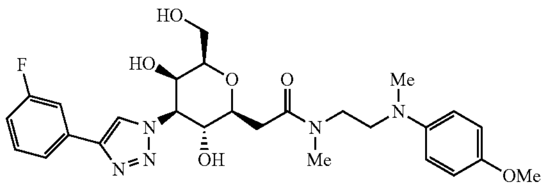 [SMILES: COc1ccc(N(C)CCN(C)C(=O)C[C@@H]2O[C@H](CO)[C@H](O)[C@H](n3cc(-c4cccc(F)c4)nn3)[C@H]2O)cc1] | | 0.17 |
| B22 | 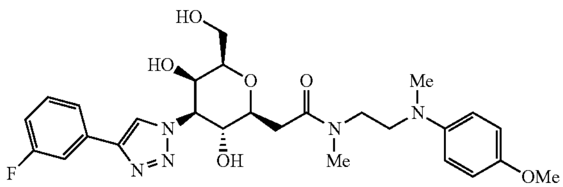 [SMILES: COc1ccc(N(C)CCN(C)C(=O)C[C@@H]2O[C@H](CO)[C@H](O)[C@H](n3cc(-c4cccc(F)c4)nn3)[C@H]2O)cc1] | | 0.31 |
| B23 | 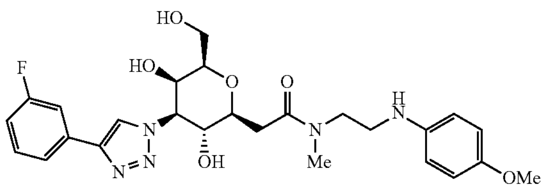 [SMILES: COc1ccc(NCCN(C)C(=O)C[C@@H]2O[C@H](CO)[C@H](O)[C@H](n3cc(-c4cccc(F)c4)nn3)[C@H]2O)cc1] | | 0.25 |
Example B24
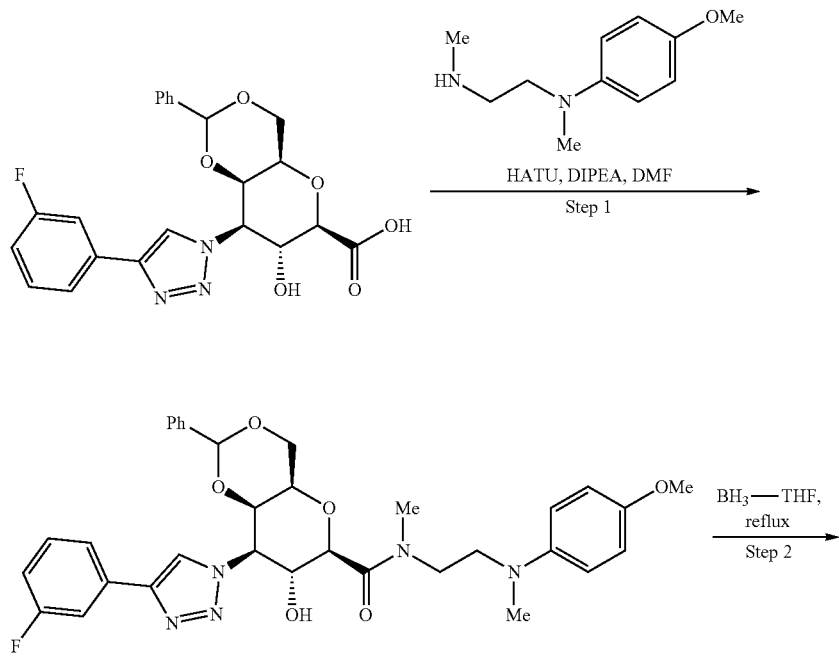

-continued
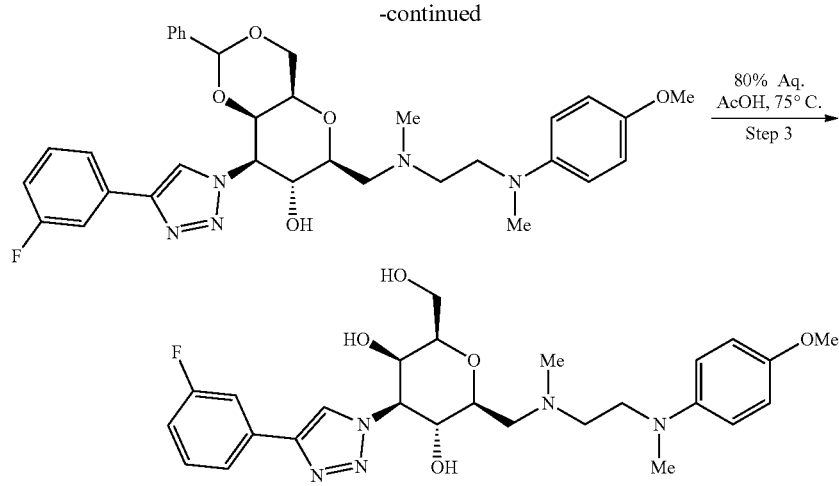
Example B24
Example B25
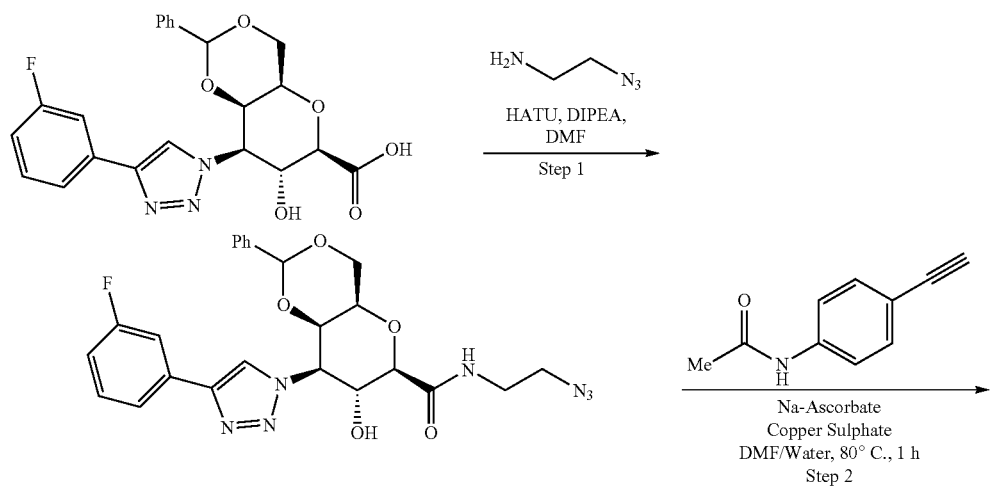
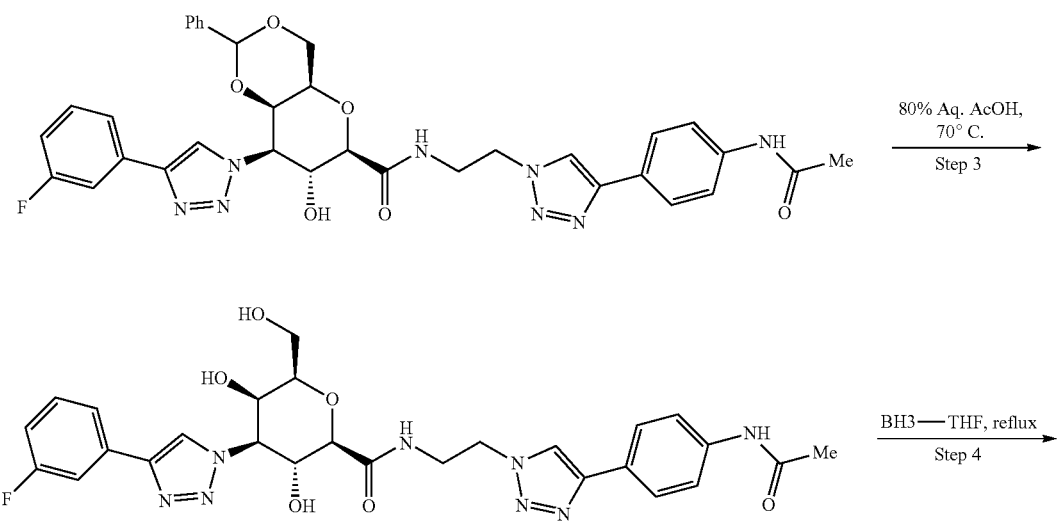

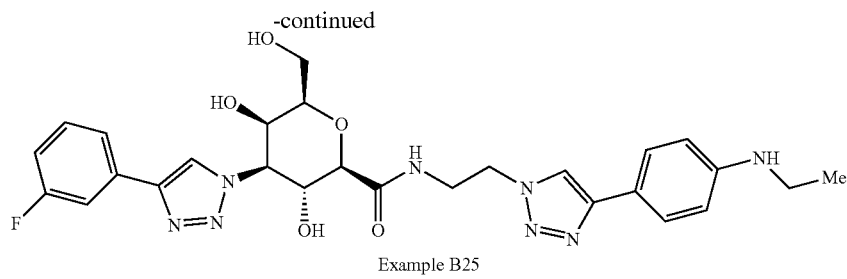

Example B25

We claim:

1. A compound of Formula (I) or (II):

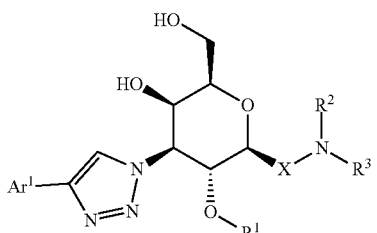

(I)

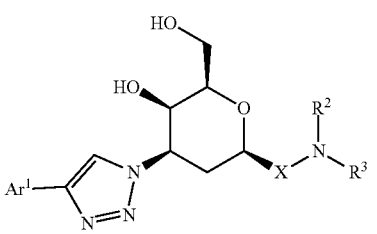

(II)

or a pharmaceutically acceptable salt thereof, wherein:

X is independently selected from —C(O)—, —CH$_2$—, and —CH$_2$C(O)—;

Ar$^1$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;

R$^1$ is independently selected from H, C$_{1-4}$ alkyl, and C$_{1-4}$ haloalkyl;

R$^2$ is independently H or C$_{1-4}$ alkyl;

R$^3$ is independently selected from Ar$^2$, —(CH$_2$)$_{1-2}$Ar$^2$, and —CH$_2$CH$_2$NR$^4$Ar$^2$;

Ar$^2$ is independently selected from a heteroaryl including from 9 to 10 ring atoms, wherein from 1 to 4 ring atoms are each independently selected from N, N(R$^5$), O, and S; and wherein each ring moiety is substituted with 0 to 4 substituents selected from OH, cyano, halogen, C$_{1-4}$ alkyl, C$_{1-4}$ haloalkyl, C$_{1-4}$ alkoxy, C$_{1-4}$ haloalkoxy, N(C$_{1-4}$ alkyl)$_2$, —SO$_2$(C$_{1-4}$ alkyl), —OPh, —OBn, C$_{3-6}$ cycloalkyl, and phenyl substituted with 0 to 1 substituent selected from cyano, halogen, C$_{1-4}$ alkyl, C$_{1-4}$ haloalkyl, C$_{1-4}$ alkoxy, C$_{1-4}$ haloalkoxy, —NH$_2$, —NH(C$_{1-4}$ alkyl), and —N(C$_{1-4}$ alkyl)$_2$;

R$^4$ is independently H or C$_{1-4}$ alkyl; and

R$^5$ is independently H or C$_{1-4}$ alkyl.

2. The compound of claim 1, wherein the compound is of Formula (Ia):

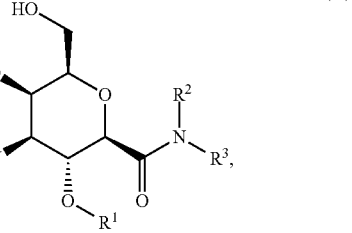

(Ia)

or a pharmaceutically acceptable salt thereof.

3. The compound of claim 2, wherein:

Ar$^1$ is independently phenyl or naphthyl; and wherein each ring moiety is substituted with 1 to 3 substituents selected from cyano, halogen, C$_{1-4}$ alkyl, and C$_{1-4}$ alkoxy;

R$^1$ is independently H or C$_{1-4}$ alkyl; and

Ar$^2$ is independently selected from benzothiophenyl, benzothiazolyl, N—(C$_{1-4}$ alkyl)-indazolyl, and quinolinyl; and wherein each ring moiety is substituted with 0 to 4 substituents selected from OH, cyano, halogen, C$_{1-4}$ alkyl, C$_{1-4}$ alkoxy, C$_{1-4}$ haloalkyl, C$_{1-4}$ haloalkoxy, N(C$_{1-4}$ alkyl)$_2$, —SO$_2$(C$_{1-4}$ alkyl), —OPh, and —OBn.

4. The compound of claim 3, wherein:

Ar$^1$ is independently selected from:

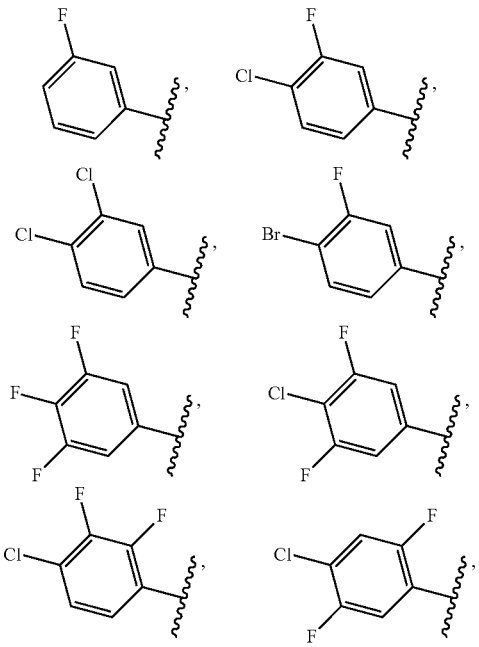

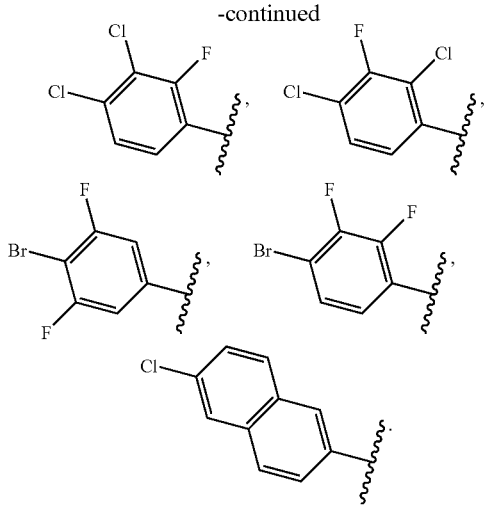
5. The compound of claim 4, wherein:
R³ is independently selected from Ar², —(CH₂)₁₋₂Ar², and —CH₂CH₂NR⁴Ar²;
Ar² is independently selected from:
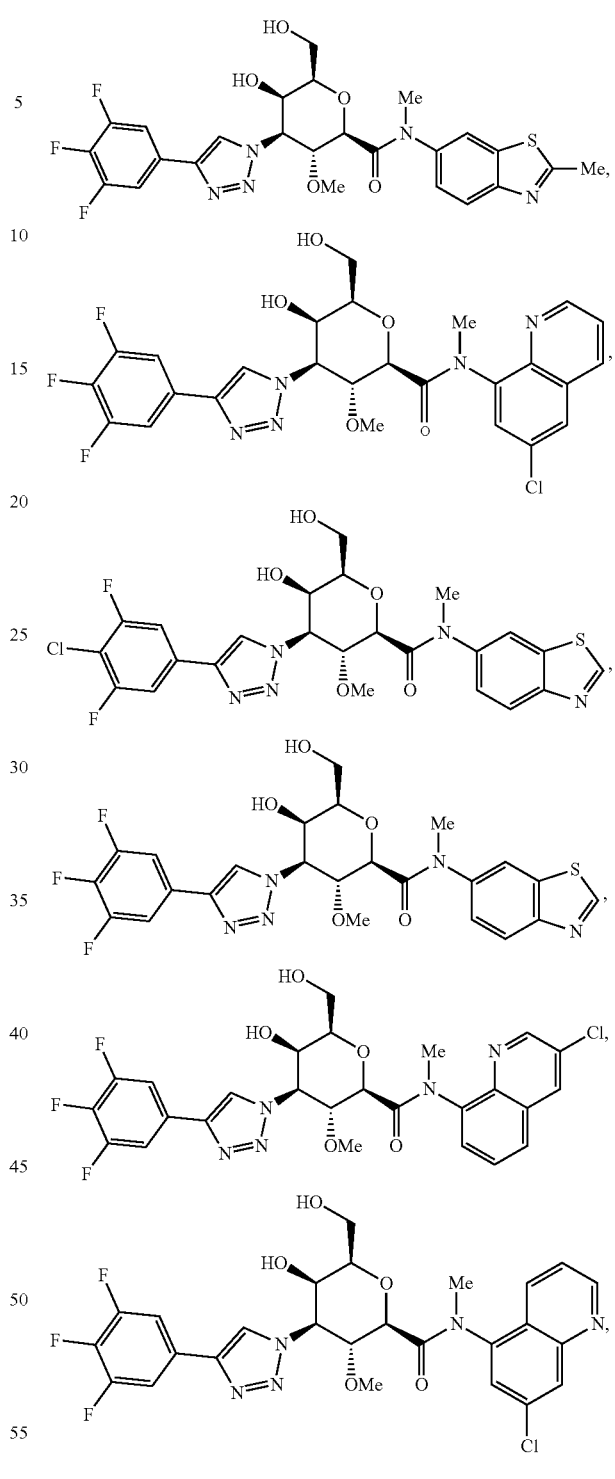
6. The compound of claim 5, wherein:
R¹ is CH₃;
R² is independently selected from: H, CH₃, —CH₂CH₃, and —CH(CH₃)₂; and
R⁴ is independently H or CH₃.
7. A compound of claim 1, wherein the compound is selected from:
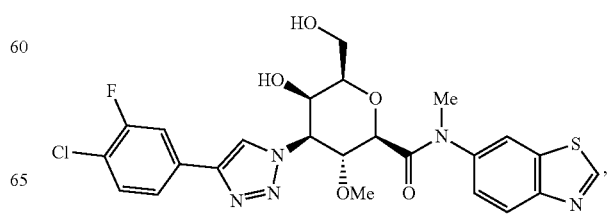

-continued
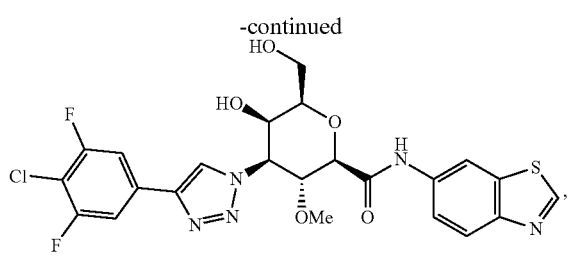
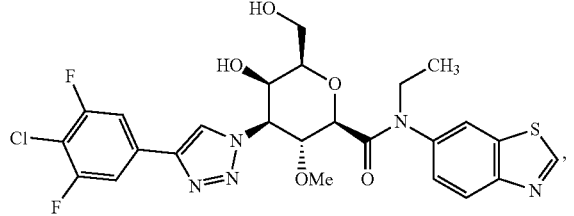
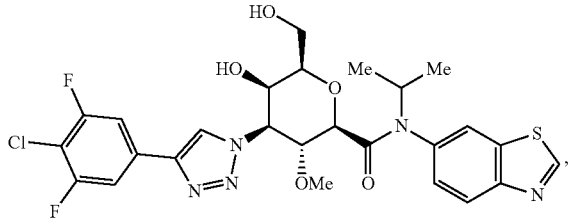
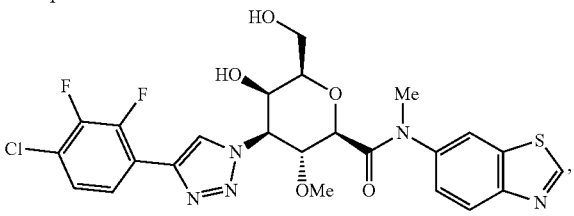
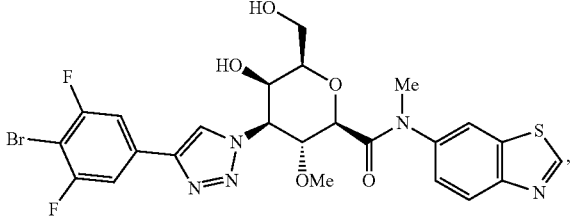
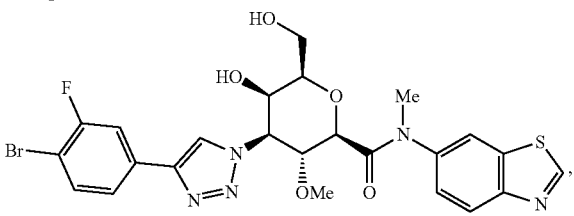
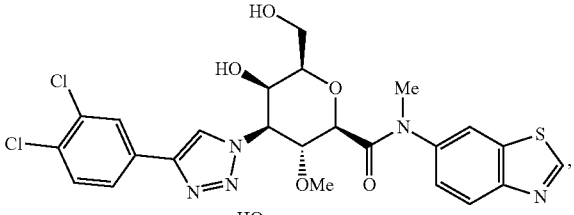
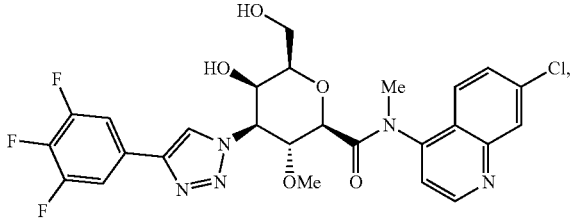
-continued
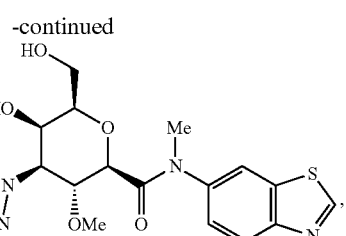
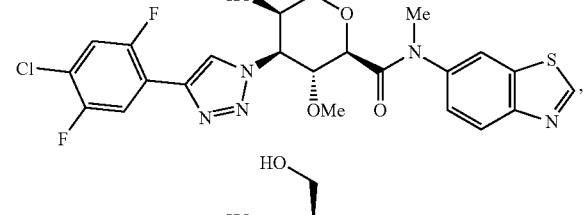
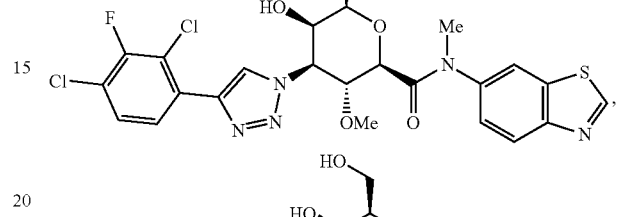
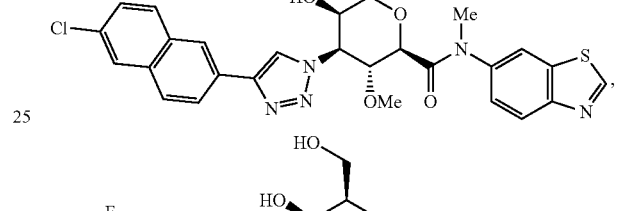
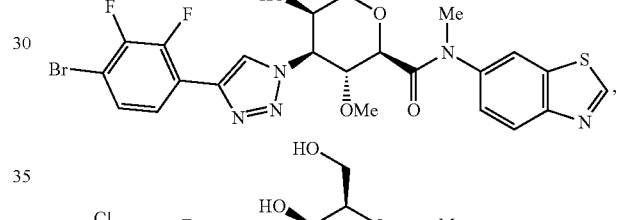
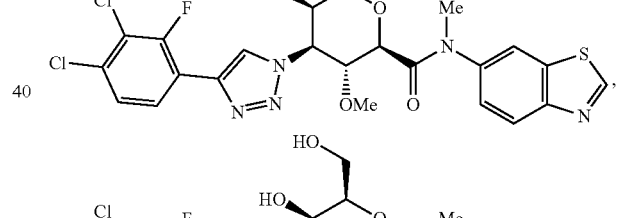
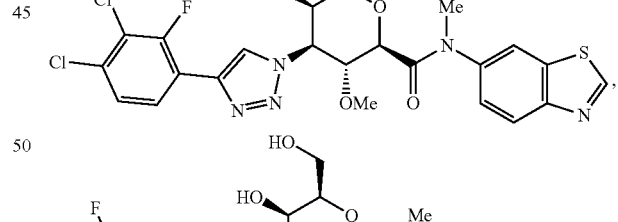
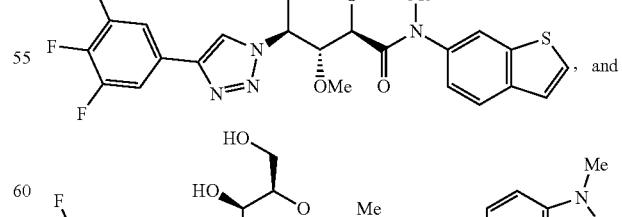, and
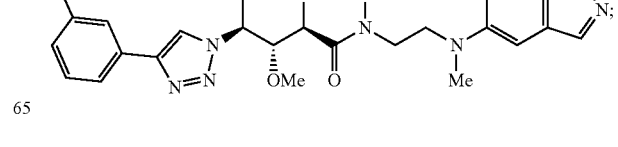
or a pharmaceutically acceptable salt thereof.

8. A composition comprising a therapeutically effective amount of a compound or a pharmaceutically acceptable salt thereof of claim 1, and one or more pharmaceutically acceptable carriers.

9. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound or a pharmaceutically acceptable salt thereof of claim 1 to a patient.

10. A method for treating a disease or condition selected from renal fibrosis, pulmonary fibrosis, hepatic fibrosis, arterial fibrosis, and systemic sclerosis; comprising administering a therapeutically effective amount of a compound of claim 1, or a pharmaceutically acceptable salt thereof of to a patient.

11. A composition comprising a therapeutically effective amount of a compound or a pharmaceutically acceptable salt thereof of claim 7, and one or more pharmaceutically acceptable carriers.

12. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound or a pharmaceutically acceptable salt thereof of claim 7 to a patient.

13. A method for treating a disease or condition selected from renal fibrosis, pulmonary fibrosis, hepatic fibrosis, arterial fibrosis, and systemic sclerosis; comprising administering a therapeutically effective amount of a compound of claim 7, or a pharmaceutically acceptable salt thereof of to a patient.

* * * * *